(12) United States Patent
Nishiyama et al.

(10) Patent No.: US 11,399,765 B2
(45) Date of Patent: Aug. 2, 2022

(54) DEMENTIA INFORMATION OUTPUT SYSTEM AND RECORDING MEDIUM

(71) Applicant: PANASONIC INTELLECTUAL PROPERTY MANAGEMENT CO., LTD., Osaka (JP)

(72) Inventors: Takashi Nishiyama, Hyogo (JP); Yoshihiro Matsumura, Osaka (JP); Kengo Abe, Nara (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 286 days.

(21) Appl. No.: 16/485,753

(22) PCT Filed: Dec. 21, 2017

(86) PCT No.: PCT/JP2017/045907
§ 371 (c)(1),
(2) Date: Aug. 13, 2019

(87) PCT Pub. No.: WO2018/150725
PCT Pub. Date: Aug. 23, 2018

(65) Prior Publication Data
US 2020/0046282 A1    Feb. 13, 2020

(30) Foreign Application Priority Data
Feb. 16, 2017    (JP) .............................. JP2017-027188

(51) Int. Cl.
*A61B 5/00*    (2006.01)
*A61B 5/11*    (2006.01)

(52) U.S. Cl.
CPC .......... *A61B 5/4088* (2013.01); *A61B 5/1118* (2013.01); *A61B 5/4806* (2013.01); *A61B 5/7275* (2013.01); *A61B 5/742* (2013.01)

(58) Field of Classification Search
CPC ... A61B 5/4806; A61B 5/4088; A61B 5/7275; A61B 5/742; A61B 5/1118; A61B 10/00
See application file for complete search history.

(56) References Cited

U.S. PATENT DOCUMENTS

2003/0216671 A1    11/2003    Saruwarati et al.
2009/0256710 A1    10/2009    Duckert et al.
(Continued)

FOREIGN PATENT DOCUMENTS

JP    2003-153868 A    5/2003
JP    2003-325488 A    11/2003
(Continued)

OTHER PUBLICATIONS

International Search Report and Written Opinion dated Mar. 13, 2018 in International Application Mo. PCT/JP2017/045907; with English translation.
(Continued)

*Primary Examiner* — Christian Jang
*Assistant Examiner* — Anna Roberts
(74) *Attorney, Agent, or Firm* — McDermott Will & Emery LLP

(57) ABSTRACT

A dementia information output system according to an aspect of the present invention includes: an acquisition unit configured to acquire an amount of body motion of a user; a determining unit configured to determine a likelihood that the user is developing a mild dementia or the like on the basis of a variability degree that is a degree by which an amount of body motion varies over a plurality of days in each of a plurality of time periods; and an outputting unit configured to output dementia information indicating the likelihood determined by the determining unit.

9 Claims, 15 Drawing Sheets

(56) References Cited

U.S. PATENT DOCUMENTS

| | | | | |
|---|---|---|---|---|
| 2015/0208975 A1* | 7/2015 | Ghajar | ............... | A61B 5/7264 |
| | | | | 600/595 |
| 2015/0245789 A1* | 9/2015 | Dromerick | ........... | A61B 5/1124 |
| | | | | 600/558 |

FOREIGN PATENT DOCUMENTS

| | | | | |
|---|---|---|---|---|
| JP | 2005-296231 A | | 10/2005 |
| JP | 2007-190306 A | | 8/2007 |
| JP | 2007190306 A | * | 8/2007 |
| JP | 2011-130836 A | | 7/2011 |
| JP | 2014-018341 A | | 2/2014 |
| JP | 2015016193 A | * | 1/2015 |
| JP | 2016-022310 A | | 2/2016 |
| JP | 2017-010182 A | | 1/2017 |
| TW | I494084 B | | 8/2015 |

OTHER PUBLICATIONS

Taiwan Intellectual Patent Office (TIPO) office action dated Sep. 19, 2018 in the corresponding Taiwan Application No. 106146440.
Office Action dated Jul. 20, 2021, issued in corresponding Chinese Patent Application No. 201780086300.8; with English translation of Search Report.
Office Action dated Jun. 3, 2022 issued in corresponding Malaysian Patent Application No. PI2019004573.

* cited by examiner

DEMENTIA INFORMATION OUTPUT SYSTEM AND RECORDING MEDIUM

CROSS-REFERENCE OF RELATED APPLICATIONS

This application is the U.S. National Phase under 35 U.S.C. § 371 of International Patent Application No. PCT/JP2017/045907, filed on Dec. 21, 2017, which in turn claims the benefit of Japanese Application No. 2017-027188, filed on Feb. 16, 2017, the entire disclosures of which Applications are incorporated by reference herein.

TECHNICAL FIELD

The present invention relates to a dementia information output system and the like that outputs dementia information.

BACKGROUND ART

Hitherto, an early-stage dementia discerning system that discerns dementia by finding an operation different from a regular operation tendency on the basis of an operating status of a switch on a watching sensor unit has been known (refer to Patent Literature (PTL) 1).

CITATION LIST

Patent Literature

PTL 1: Japanese Unexamined Patent Application Publication No. 2014-018341

SUMMARY OF THE INVENTION

Technical Problems

The early-stage dementia discerning system disclosed in PTL 1 determines whether a subject (user) has the dementia on the basis of an additional work with respect to a daily work of the subject. For example, on the basis of an additional work in which the subject operates the switch on the watching sensor unit upon awakening every day, whether the subject has dementia is determined in accordance with whether the subject forgets to perform the additional work.

An object of the present invention is to provide a dementia information output system capable of outputting dementia information indicating the likelihood of mild dementia and the like without the need of an additional work with respect to a daily work. Another object of the present invention is to provide a recording medium having a control program (a program for computers) recorded thereon for use in the dementia information output system.

Note that the term "mild dementia and the like" is used herein to refer to the concept encompassing mild dementia and mild cognitive impairment (MCI) which precedes the mild dementia. The mild dementia and the like may be herein simply referred to as dementia or mild dementia. The mild dementia and the like are distinguished from the state of being healthy and normal.

Solutions to Problems

In order to achieve the aforementioned objects, a dementia information output system according to an aspect of the present invention includes: an acquisition unit configured to acquire an amount of body motion of a user; a determining unit configured to determine a likelihood that the user is developing a mild dementia or the like on the basis of a variability degree that is a degree by which the amount of body motion varies over a plurality of days in each of a plurality of time periods; and an outputting unit configured to output dementia information indicating the likelihood determined by the determining unit.

In addition, a non-transitory computer-readable recording medium according to an aspect of the present invention is a non-transitory computer-readable recording medium having a control program recorded thereon for causing an apparatus including a microprocessor to execute dementia information output processing. The dementia information output processing includes: an acquisition step of acquiring an amount of body motion of a user; a determination step of determining a likelihood that the user is developing a mild dementia or the like on the basis of a variability degree that is a degree by which the amount of body motion varies over a plurality of days in each of a plurality of time periods; and an output step of outputting dementia information indicating the likelihood determined in the determination step.

Advantageous Effect of Invention

The dementia information output system and the like according to an aspect of the present invention is capable of determining the likelihood of the mild dementia and the like even when the additional work with respect to the daily work is not performed.

DESCRIPTION OF EXEMPLARY EMBODIMENTS

Underlying Knowledge of Invention

Figure 1:
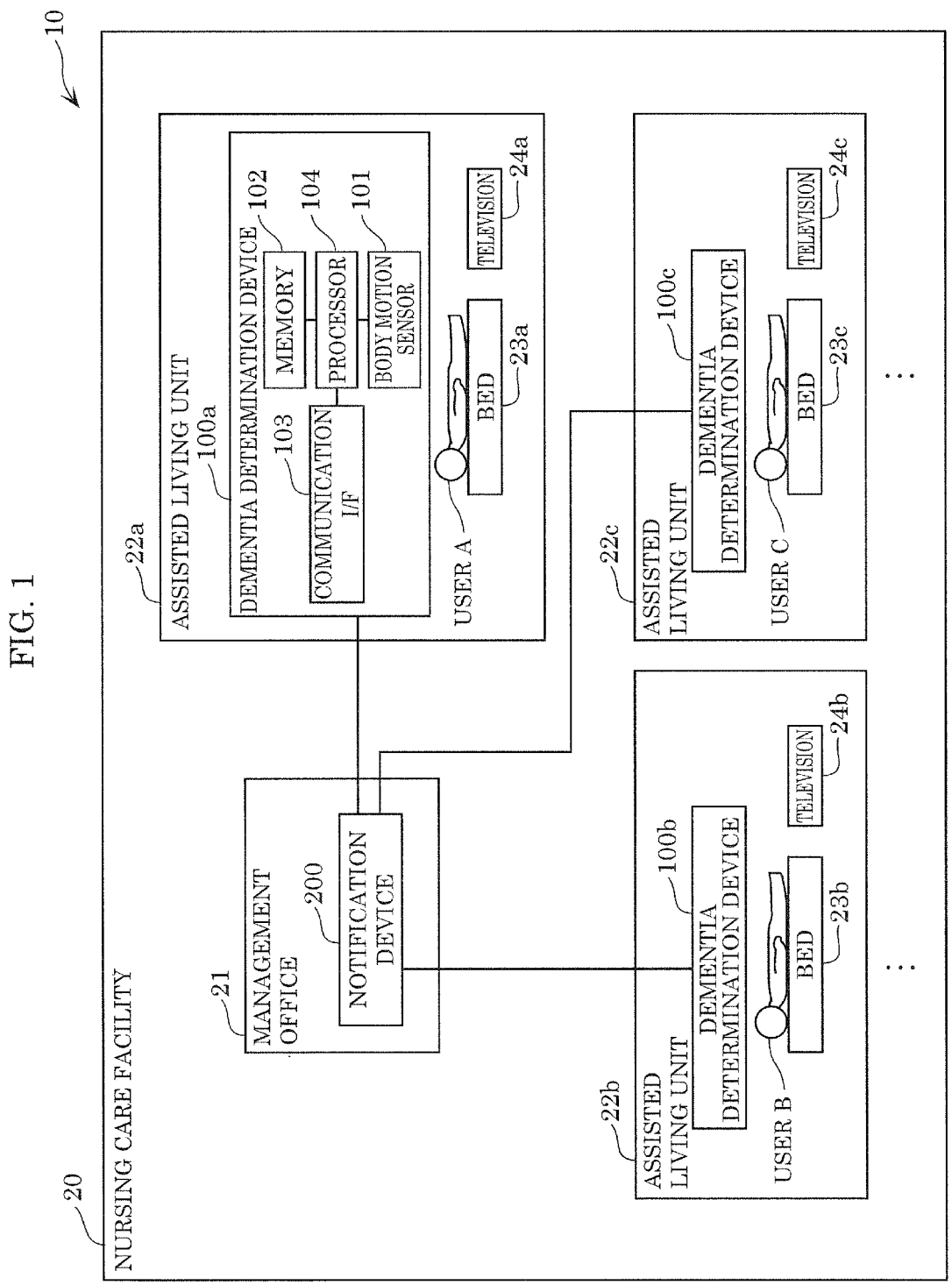
FIG. 1 is a schematic configuration view illustrating an example of a configuration of a dementia information output system according to Embodiment 1.

In the aging society, problems concerning dementia elderlies are predicted to become visible. In particular, in recent years, accidents involving cases where a car driven by a dementia elderly travels in the wrong direction on a highway or runs on a sidewalk are reported in news reports many times, and television programs relating to dementia are frequently aired.

There are various levels of dementia from a mild level to a severe level. When abnormality is found in the stage of a mild cognitive impairment preceding dementia, there is a possibility that the development of dementia can be suppressed by exercise training and the like. Therefore, the act of finding abnormalities early in the stage of the mild cognitive impairment is drawing attention. As a method of finding abnormalities in an early stage, there is a method in which the subject notices abnormalities by him/herself, or a method in which the people around the subject notice the abnormalities.

Further, the method in which the people around the subject notice the abnormalities includes a method in which the people around the subject notice abnormalities in the way the subject talks, and a method in which the people around the subject notice abnormalities in the life behavior of the subject. In particular, the method in which the people around the subject notice abnormalities in the life behavior of the subject is described here.

Specifically, when the subject develops Alzheimer-type dementia, the subject develops a circadian disorder. For example, it is assumed that the daytime activity level of the subject decreases, thereby causing the subject to doze off even during the daytime, and hence the subject sleeps shallowly in the nighttime.

Patients with dementia are assumed to have a wide and severe organic disorder over the hypothalamus and the brainstem which control the biological clock for sleeping, awakening, and the like. In particular, for patients with Alzheimer-type dementia, the sleeping hours of a day are divided into a large number of time periods, and a case where a sleep-wake cycle is frequently repeated in the nighttime time period may be repeated almost every day.

In addition, if the subject is in the state of being healthy and normal, the subject is assumed to live a life that is stable to a certain degree in accordance with a pattern in which the subject wakes up around the same point in time, lives actively during the daytime, goes to bed around the same point in time, and sleeps deeply during the nighttime. Meanwhile, when the subject develops dementia, the subject dozes off during the daytime, and hence may wake up during the nighttime. Further, it is assumed that a situation in which it is difficult to predict the time the subject dozes off during the daytime and the time the subject wakes up during the nighttime continues, the point in time of waking up in the morning, the nap time, and the point in time of going to bed in the night become inconsistent, and the life pattern of a day becomes unstable.

According to the above knowledge and so on, the technical concept of a dementia information output system capable of outputting dementia information indicating the likelihood of mild dementia and the like on the basis of the variability degree (instability degree) of the life pattern has been created. Hereinafter, embodiments of the dementia information output system are described with reference to the drawings.

Each of the embodiments herein shows a specific example of the present invention. Thus, the numerical values, shapes, materials, structural elements, and the arrangement and connection of the structural elements, steps, the processing order of the steps, and the like shown in the following embodiments are mere examples, and are not intended to limit the present invention. Among the structural elements in the following embodiments, structural elements not recited in independent claims can be arbitrarily included.

In addition, the figures are schematic diagrams and are not necessarily precise illustrations. In particular, the graphs do not necessarily indicate the exact values.

Embodiment 1

Dementia information output system 10 according to this embodiment is described below.

Configuration

Dementia information output system 10 is a system that determines the likelihood that a subject (user) such as an elderly or a person in need of assistance is developing the mild dementia and the like (whether the subject (user) is developing the mild dementia and the like, for example), and outputs dementia information indicating the likelihood that the user is developing the mild dementia and the like.

For example, dementia information output system 10 determines the likelihood that the user is developing the mild dementia and the like on the basis of a variability degree that is the degree by which the amount of body motion varies over a plurality of days in each of a plurality of time periods. The variability degree corresponds to an instability degree that is the degree by which the amount of body motion is unstable over a plurality of days in each of the plurality of time periods, and corresponds to the variability degree (instability degree) of the life pattern.

FIG. 1 is a schematic configuration view illustrating an example of dementia information output system 10 according to Embodiment 1. As illustrated in this figure, dementia information output system 10 includes dementia determination devices 100a to 100c and notification device 200. Although three dementia determination devices 100a to 100c are illustrated herein for convenience, dementia information output system 10 may include any number of dementia determination devices which is not less than one.

In FIG. 1, dementia information output system 10 applied to nursing care facility (facility covered by long-term care insurance) 20 such as an elderly nursing facility or a nursing and medical treatment home for the aged is exemplified. In dementia information output system 10, dementia determination devices 100a to 100c determine the mild dementia and the like for users A to C living in assisted living units 22a to 22c of nursing care facility 20, and dementia information indicating the determination result and the like is sent to notification device 200.

Notification device 200 is installed, for example, in management office 21 in which a caretaker such as a care worker, a nurse, a doctor, or the like is mainly present. The caretaker or the like can easily grasp the dementia information (the information about the likelihood that the user is developing the mild dementia and the like) about users A to C respectively living in assisted living units 22a to 22c by notification device 200, and can appropriately provide necessary treatment and the like.

Assisted living unit 22a is a room which includes bed 23a, television 24a, and the like and in which user A lives. Dementia determination device 100a is installed in assisted living unit 22a. Likewise, assisted living units 22b and 22c are rooms which include beds 23b and 23c, televisions 24b and 24c, dementia determination devices 100b and 100c, and the like and in which users B and C live, respectively.

Dementia determination device 100a is an information processing device (computer) that determines whether user A has the mild dementia and the like, for example, on the basis of the variability degree (instability degree) of the life pattern of user A, and transmits dementia information including the determination result. Dementia determination device 100a includes body motion sensor 101, memory 102, communication interface (communication I/F) 103, and processor (microprocessor) 104.

Although dementia determination device 100a installed in assisted living unit 22a of user A is mainly described herein, dementia determination devices 100b and 100c also include configurations similar to that in dementia determination device 100a.

Body motion sensor 101 is a sensor for sensing the body motion of user A. Body motion sensor 101 may be any sensor as long as the sensor can sense the body motion of user A.

For example, body motion sensor 101 is a radio-frequency sensor including a transmission and reception circuit that sends (transmits) radio waves (for example, microwaves) and receives reflected waves in order to measure the motion of human bodies. In order to measure the body motion of user A, body motion sensor 101 may be installed, for example, on bed 23a (for example, a part of the bottom located under a mattress), or a ceiling part above bed 23a in assisted living unit 22a.

In addition, body motion sensor 101 may be placed next to a pillow on bed 23a, and may sense the body motion of user A by sensing the vibration of bed 23a. In addition, body motion sensor 101 may be carried by user A, and may sense the body motion of user A by sensing the vibration associated with the body motion of user A. When user A frequently gets out of assisted living unit 22a, body motion sensor 101 carried by user A is effective.

In addition, body motion sensor 101 may include a camera installed in assisted living unit 22a. Further, body motion sensor 101 may sense the body motion of user A on the basis of a video acquired from the camera.

In addition, body motion sensor 101 may be implemented by a combination of a plurality of elements described above. For example, body motion sensor 101 may be a combination of a sensor that is carried by user A and senses the body motion of user A by sensing the vibration associated with the body motion of user A, and a sensor that includes a camera and senses the body motion of user A on the basis of a video acquired from the camera.

Memory 102 is, for example, a read-only memory (ROM) in which a program and data are held in advance or a random-access memory (RAM) which is used to save data and the like upon execution of a program. Memory 102 may include a non-volatile memory, for example.

Communication I/F 103 is a communication circuit for communicating with notification device 200. The communication between dementia determination device 100a and notification device 200 may be wireless communication or may be wired communication.

Processor 104 performs a process of controlling communication I/F 103 and the like by executing a control program stored in memory 102. Note that dementia determination device 100a may include, for example, a display such as a liquid-crystal display (LCD), and may display the dementia information on the display.

Notification device 200 installed in management office 21 is a monitoring device including a communication interface and a display, and may be a computer (information processing device) including a memory and a processor, for example.

Figure 2:
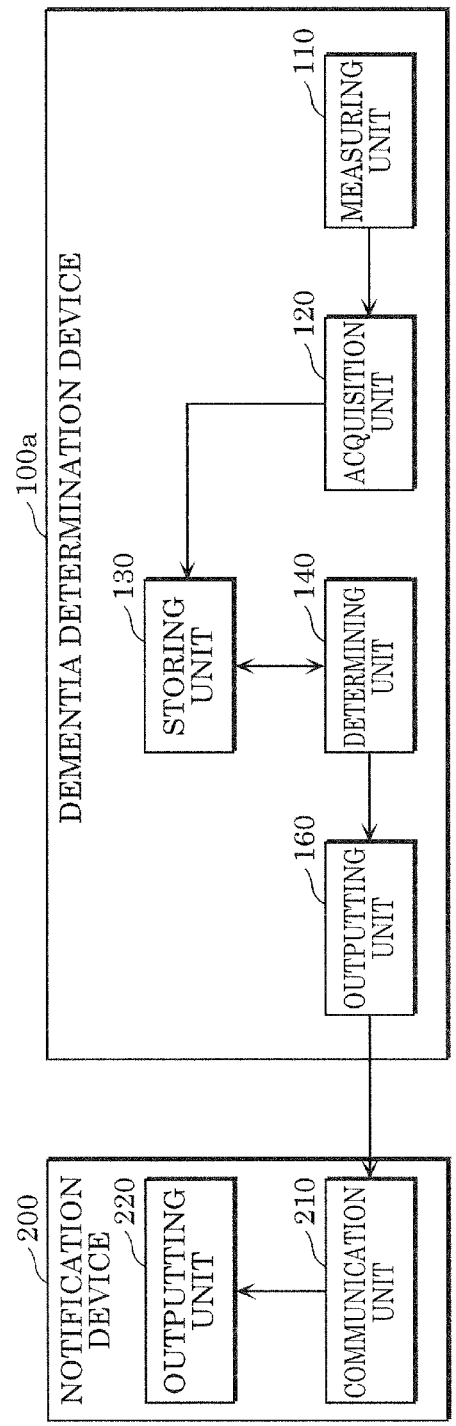
FIG. 2 is a block diagram illustrating a configuration of a dementia determination device and the like according to Embodiment 1.

FIG. 2 is a block diagram illustrating a configuration of dementia determination device 100a of dementia information output system 10 according to Embodiment 1. Dementia determination device 100a is installed in assisted living unit 22a in which user A lives. Note that, in this figure, a configuration of notification device 200 installed in management office 21 is also illustrated.

Dementia determination device 100a including hardware elements illustrated in FIG. 1 outputs the dementia information on the basis of the variability degree (instability degree) of the life pattern of user A. Therefore, dementia determination device 100a includes measuring unit 110, acquisition unit 120, storing unit 130, determining unit 140, and outputting unit 160 as configuration elements as illustrated in FIG. 2.

Measuring unit 110 is implemented by body motion sensor 101, processor 104 that executes the control program, and the like, and is a measuring instrument that measures the body motion of user A with use of body motion sensor 101. By using body motion sensor 101, measuring unit 110 may specify, on a per-minute basis, the amount of body motion that is the degree of the body motion expressed using ten stages of values from 0 (the minimum value such as no body motion) to 9 (maximum value), for example.

Acquisition unit 120 is implemented by processor 104 that executes the control program and the like, and is an acquisition instrument that acquires the amount of body motion of user A. For example, acquisition unit 120 acquires the amount of body motion accumulated in each time period by acquiring the amount of body motion from measuring unit 110 and aggregating the amount of body motion for each time period. Specifically, the length of each time period is 12 hours or less. In addition, the length of each time period is preferably 1 hour or more, bur may be 30 minutes, for example.

Storing unit 130 is implemented by regions of memory 102 and the like, and is a storage instrument for storing the amount of body motion of user A each day and each time period. For example, the amount of body motion acquired by acquisition unit 120 is accumulated in storing unit 130.

Determining unit 140 is implemented by memory 102, processor 104 that executes the control program, and the like. Determining unit 140 is a determination instrument that determines the likelihood that user A is developing the mild dementia and the like on the basis of the variability degree that is the degree by which the amount of body motion of user A varies over the plurality of days in each of the plurality of time periods. The variability degree corresponds to the degree by which the life pattern of user A varies over the plurality of days.

FIG. 3A, FIG. 3B, FIG. 4A, and FIG. 4B are graphs indicating the amount of body motion in each time period. Specifically, FIG. 3A indicates the amount of body motion of a healthy subject (a subject in a state of being healthy and normal) in each time period of a day, and FIG. 3B indicates the amount of body motion of the healthy subject in each time period of another day. In addition, FIG. 4A indicates the amount of body motion of a dementia subject (a patient with the mild dementia and the like) in each time period of a day, and FIG. 4B indicates the amount of body motion of the dementia subject in each time period of another day. Note that, the healthy subject may be user A in the state of being healthy and normal, and the dementia subject may be user A in the state of developing the mild dementia and the like.

Figure 3A:
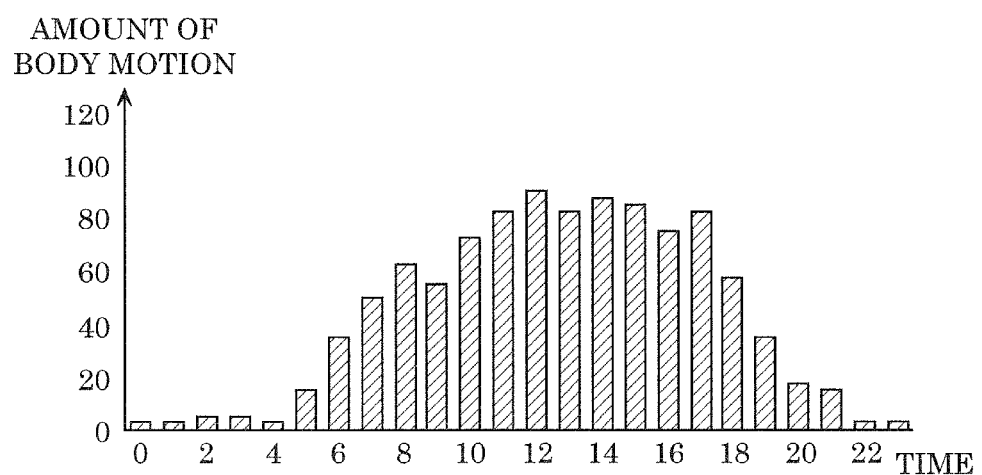
FIG. 3A is a graph indicating the amount of body motion of a healthy subject in each time period of a day.
Figure 3B:
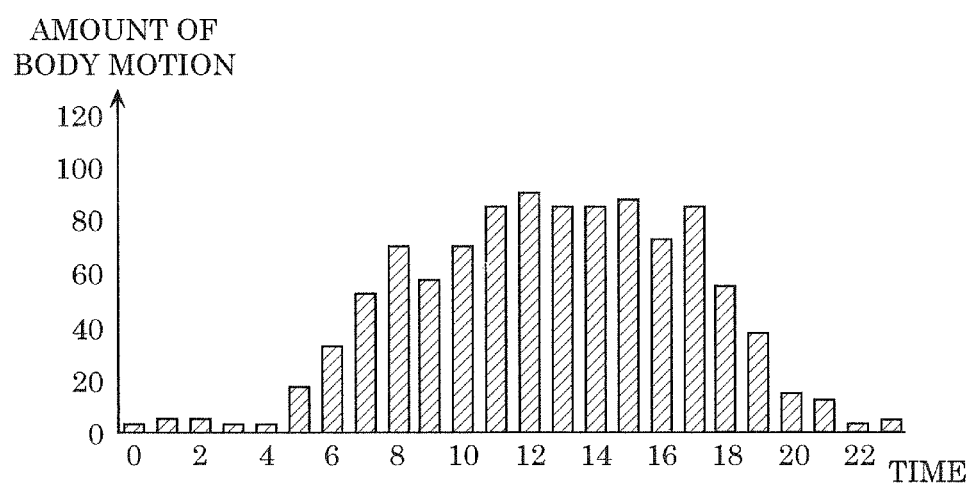
FIG. 3B is a graph indicating the amount of body motion of the healthy subject in each time period of another day.
Figure 4A:
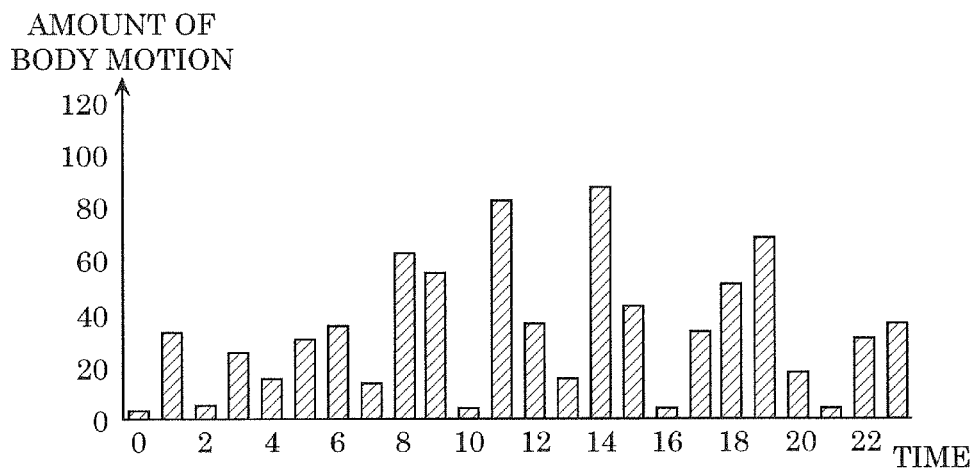
FIG. 4A is a graph indicating the amount of body motion of a dementia subject in each time period of a day.
Figure 4B:
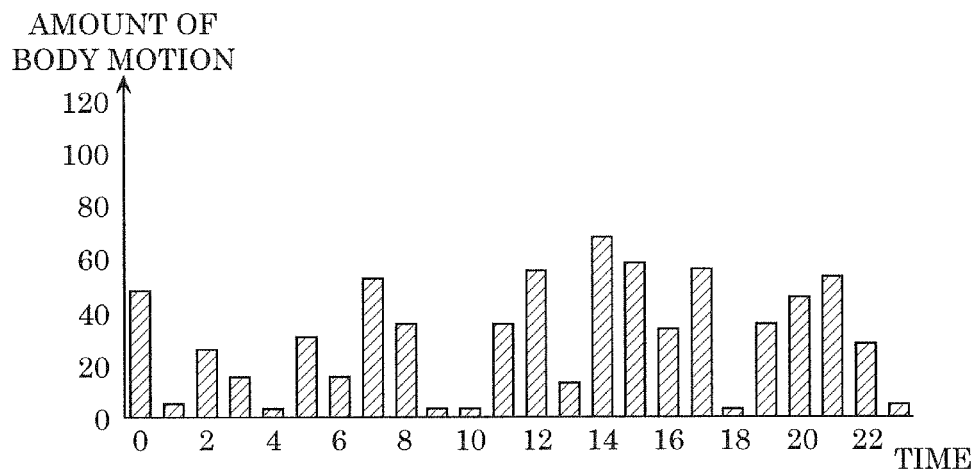
FIG. 4B is a graph indicating the amount of body motion of the dementia subject in each time period of another day.

As in FIG. 3A and FIG. 3B, the amount of body motion is clearly different between the activity during the day and the sleep during the night for the healthy subject. Further, the variability of the amount of body motion in each time period is small between two different days, and the life pattern is stable. Meanwhile, as in FIG. 4A and FIG. 4B, for the dementia subject, the amount of activity during the day is small, and body motion is generated due to awakening during the night. Further, the variability of the amount of body motion in each time period is large between two different days, and the life pattern is unstable.

Therefore, determining unit 140 determines the likelihood that user A is developing the mild dementia and the like to be higher as the abovementioned the variability degree is larger.

Outputting unit 160 is implemented by processor 104 that executes the control program, communication I/F 103, and the like. Outputting unit 160 is an output instrument that outputs the dementia information indicating the likelihood that user A is developing the mild dementia and the like. The dementia information indicates that user A is developing the mild dementia and the like when it is determined by determining unit 140 that user A is developing the mild dementia and the like. Note that, when determining unit 140 determines that user A is not developing the mild dementia and the like, outputting unit 160 does not necessarily need to output the dementia information.

In addition, for example, outputting unit 160 outputs the dementia information by transmitting the dementia information to notification device 200. Notification device 200 displays the dementia information on the display and the like by outputting unit 220 on the basis of the dementia information received by communication unit 210. In addition, when dementia determination device 100a includes a display, outputting unit 160 of dementia determination device 100a may output the dementia information by displaying the dementia information on the display.

Operation

The operation of dementia determination device 100a in dementia information output system 10 including the above-mentioned configuration is described below.

Figure 5:
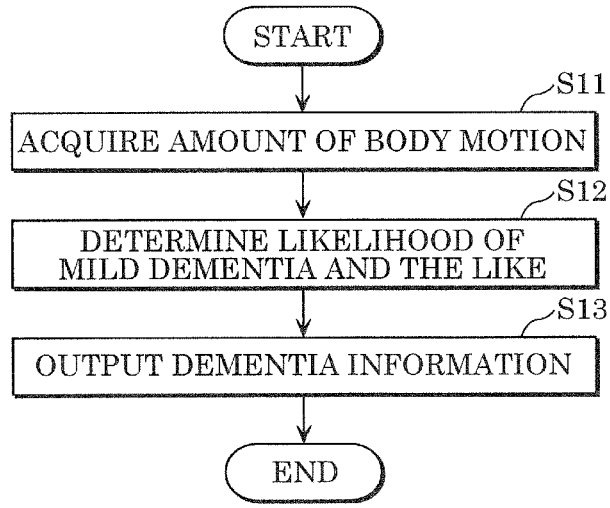
FIG. 5 is a flowchart illustrating dementia information output processing according to Embodiment 1.

FIG. 5 is a flowchart illustrating dementia information output processing according to this embodiment. The dementia information output processing is described below with reference to this figure.

In dementia determination device 100a, measuring unit 110 measures the body motion of user A, and acquisition unit 120 acquires the measurement result of the body motion from measuring unit 110 as the amount of body motion of user A and stores the amount of body motion of user A in storing unit 130 (S11).

Then, determining unit 140 refers to storing unit 130, and determines the likelihood that user A is developing the mild dementia and the like on the basis of the variability degree that is the degree by which the amount of body motion of user A varies over the plurality of days in each of the plurality of time periods (S12). Further, outputting unit 160 outputs the dementia information indicating the likelihood that user A is developing the mild dementia and the like (S13).

Figure 6:
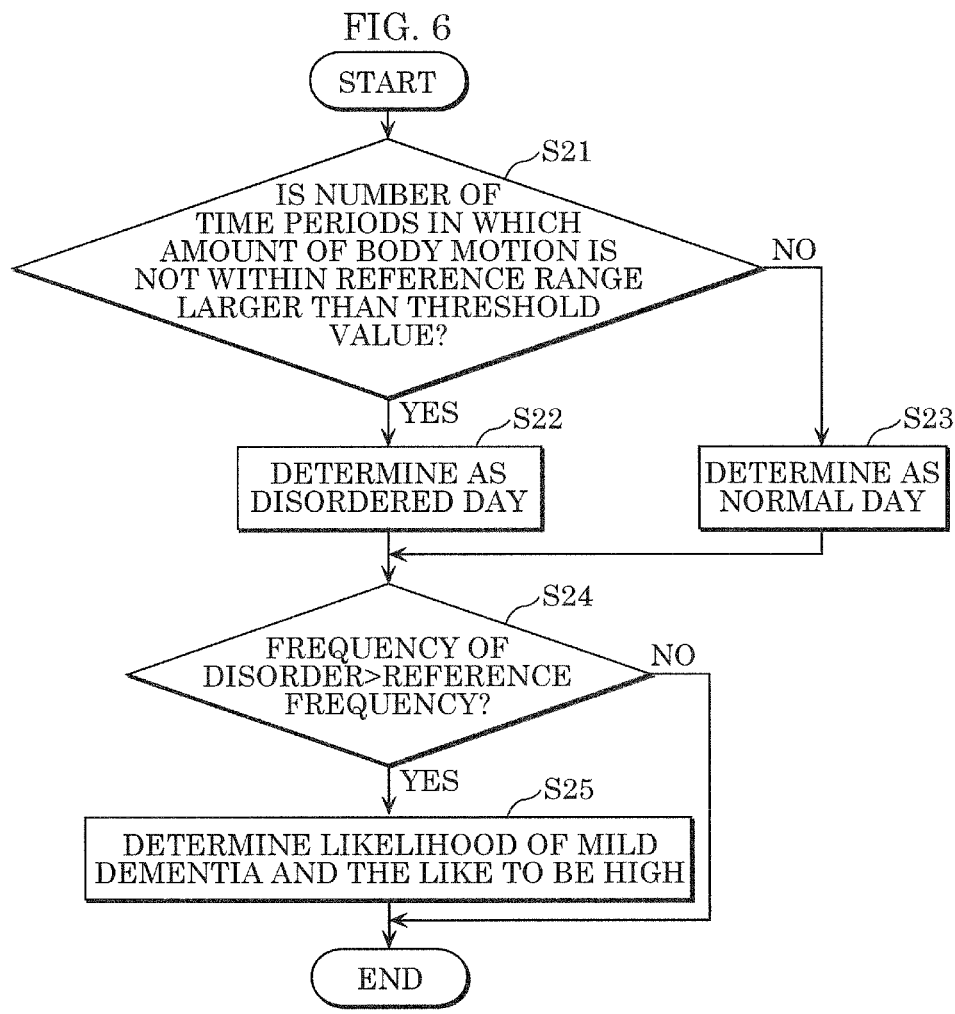
FIG. 6 is a flowchart illustrating dementia determination processing according to Embodiment 1.

FIG. 6 is a flowchart illustrating dementia determination processing according to this embodiment. The dementia determination processing corresponds to the processing performed as the dementia determination processing (S12) illustrated in FIG. 5. The dementia determination processing is described below with reference to this figure.

Determining unit 140 of dementia determination device 100a determines whether the number of the time periods in which the amount of body motion is not within the reference range is larger than a threshold value on the basis of the amount of body motion on the examination day (S21). Further, when the number of the time periods in which the amount of body motion is not within the reference range is larger than the threshold value (Yes in S21), determining unit 140 determines the examination day to be a disordered day (S22). Meanwhile, when the number of the time periods in which the amount of body motion is not within the reference range is not larger than the threshold value (No in S21), determining unit 140 determines the examination day to be a normal day (S23).

Determining unit 140 may reflect the determination result in storing unit 130. That is, determining unit 140 may store the determination result of whether the examination day is a disordered day in storing unit 130. In addition, determining unit 140 may store information indicating the number of the time periods in which the amount of body motion is not within the reference range in storing unit 130. Determining unit 140 repeats the abovementioned processing (S21 to S23) for a plurality of examination days.

Next, determining unit 140 determines whether the frequency of disorder that is the occurrence frequency of the disordered day is higher than the reference frequency (S24). Further, when the frequency of disorder is higher than the reference frequency (Yes in S24), determining unit 140 determines the likelihood of the mild dementia and the like to be higher than the case where the frequency of disorder is not higher than the reference frequency (No in S24) (S25).

For example, determining unit 140 determines that user A is developing the mild dementia and the like when the frequency of disorder is higher than the reference frequency (Yes in S24), and determines that user A is not developing the mild dementia and the like when the frequency of disorder is not higher than the reference frequency (No in S24).

The reference range (the reference range in S21) for determining whether the number of the time periods in which the amount of body motion is not within the reference range is larger than the threshold value is defined on the basis of the amount of body motion in a plurality of reference days. The plurality of reference days are a plurality of days preceding the examination day. The plurality of reference days may be selected from a plurality of days preceding the examination day excluding the days determined to be the disordered day. More specifically, the plurality of reference days may be a plurality of days out of a plurality of days from a day one month before the examination day to a day before the examination day excluding the days determined to be the disordered day.

The variability of the amount of body motion over a plurality of days affects whether the amount of body motion on the examination day is within the reference range based on the amount of body motion in the plurality of reference days. For example, when the variability of the amount of body motion over the plurality of days is large, the likelihood of the amount of body motion on the examination day not being within the reference range based on the amount of body motion in the plurality of reference days is high. Meanwhile, when the variability of the amount of body motion over the plurality of days is small, the likelihood of the amount of body motion on the examination day being within the reference range based on the amount of body motion in the plurality of reference days is high.

Therefore, determining unit 140 can determine the likelihood of the mild dementia and the like on the basis of the variability of the amount of body motion over the plurality of days by determining the likelihood of the mild dementia and the like on the basis of whether the amount of body motion on the examination day is within the reference range based on the amount of body motion in the plurality of reference days. Further, at least one of the number of the time periods in which the amount of body motion is not within the reference range and the frequency of disorder based on the number corresponds to the degree (that is, the variability degree) by which the amount of body motion varies over the plurality of days in each of the plurality of time periods.

Figure 7:
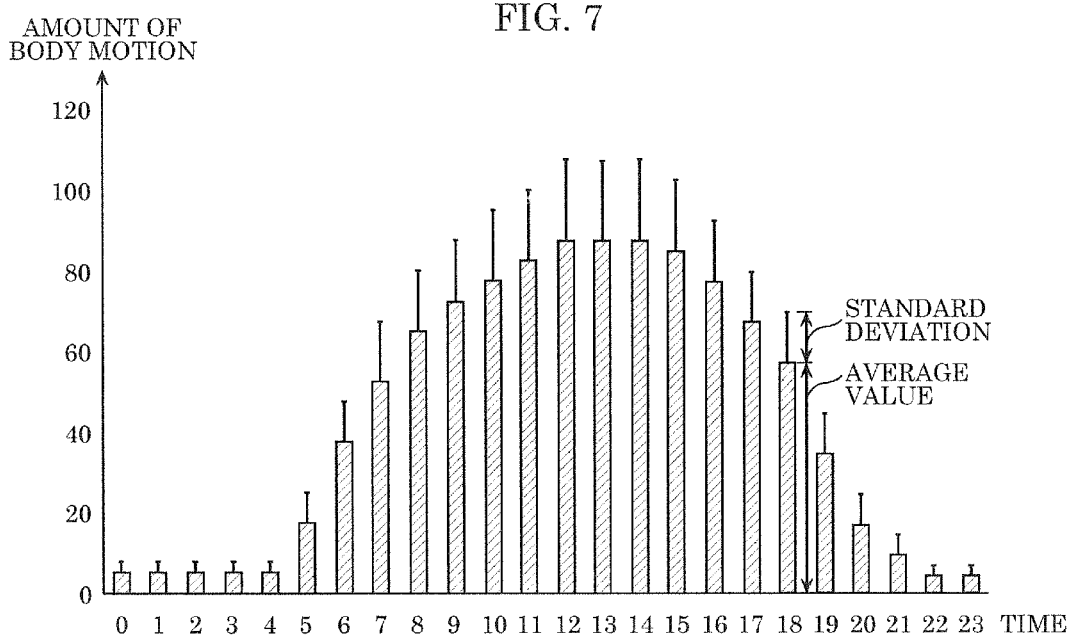
FIG. 7 is a graph for describing a reference range based on a standard deviation of the amount of body motion.

FIG. 7 is a graph for describing a reference range based on a standard deviation of the amount of body motion. FIG. 7 indicates the average value and the standard deviation of the amount of body motion in each time period in the plurality of reference days. The standard deviation is a statistic in statistics and is the positive square root of the variance.

The reference range is defined for each time period on the basis of the average value and the standard deviation of the amount of body motion in the plurality of reference days, for example. Note that determining unit 140 may define (specify) the reference range. The reference range may be defined as a range of $m \pm 3\sigma$ for each time period on the basis of an average value m and a standard deviation $\sigma$. In this case, determining unit 140 determines whether the examination day is a disordered day by determining whether the amount of body motion in each time period of the examination day is within the range of $m \pm 3\sigma$, and determining whether the number of the time periods in which the amount of body motion is not within the range of $m \pm 3\sigma$ is larger than the threshold value.

The range of $m \pm 3\sigma$ is an example of a reference range based on the standard deviation. The reference range may be a range of $m \pm \sigma$, or may be a range of $m \pm 2\sigma$. In addition, the reference range may be defined as a range of $m \pm a\sigma$ with use of a satisfying a>0.

Figure 8:
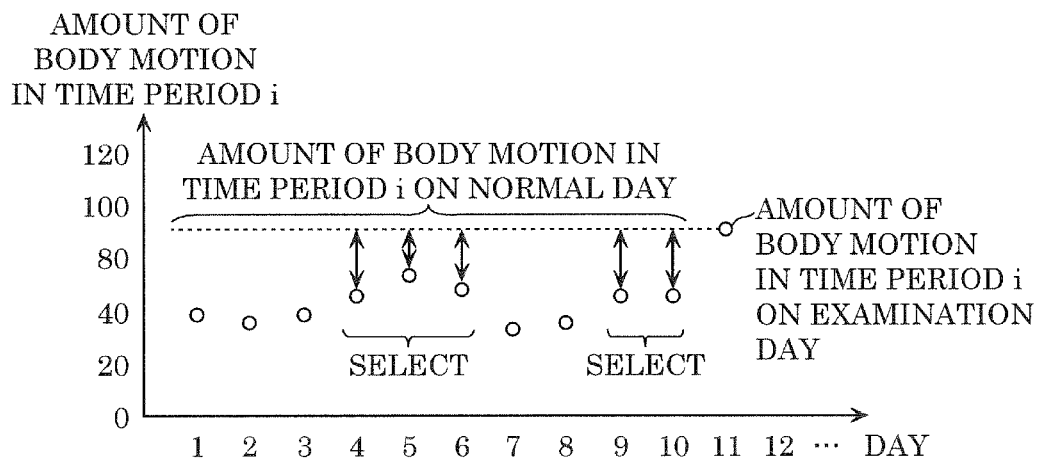
FIG. 8 is a graph for describing a reference range based on the amount of body motion and a k-nearest neighbor algorithm.

FIG. 8 is a graph for describing the reference range based on the amount of body motion and a k-nearest neighbor algorithm. The reference range may be defined on the basis of the k-nearest neighbor algorithm.

For example, determining unit 140 selects a number of k reference days from a plurality of days preceding the examination day by prioritizing the days in which the amount of body motion is close to that of the examination day for each time period i. Specifically, for example, determining unit 140 selects five reference days from ten days from a day ten days before the examination day to a day before the examination day by prioritizing the days in which the amount of body motion in the time period i is close to that of the examination day. The day determined to be the disordered day may be excluded from the selection.

Further, determining unit 140 defines the reference range on the basis of the average value of the amount of body motion in the number of k selected reference days for each time period i. Specifically, determining unit 140 defines a range of $m \pm c$ as the reference range on the basis of the average value m and an allowable error c. As a result, determining unit 140 can define the reference range, as appropriate, regardless of whether the amount of body motion is in accordance with a normal distribution.

Figure 9:
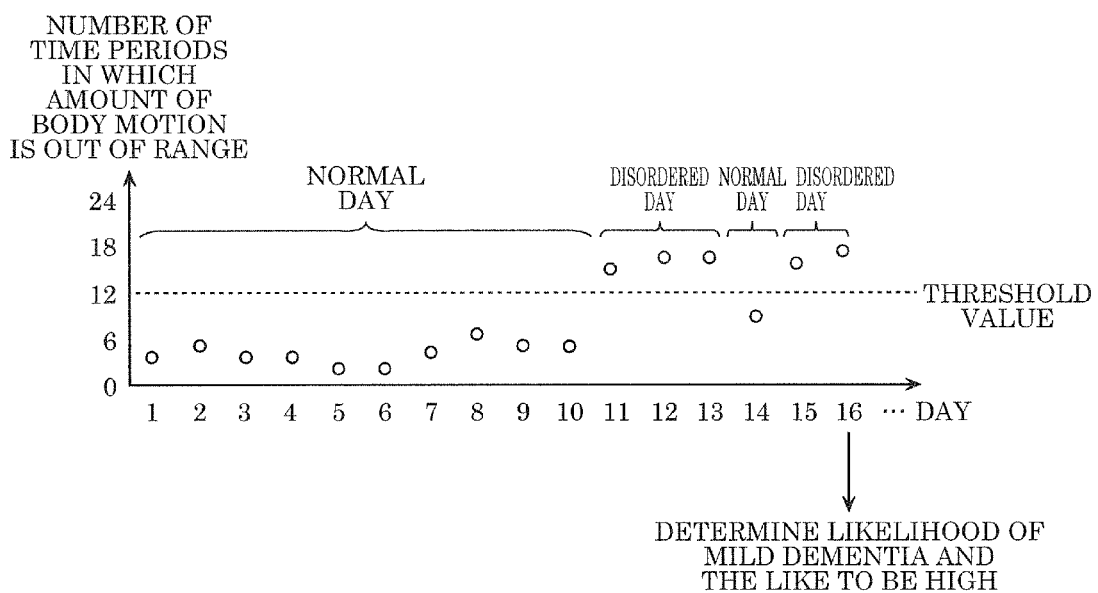
FIG. 9 is a schematic view illustrating the frequency of disorder based on the amount of body motion in each time period.

FIG. 9 is a schematic view illustrating the frequency of disorder based on the amount of body motion in each time period. Determining unit 140 determines the examination day to be a disordered day when the number of the time periods in which the amount of body motion is not within the reference range is larger than the threshold value for each of the plurality of examination days. The threshold value may be determined in accordance with a ratio to the total number of the time periods. For example, the threshold value may be half the number of the total number of the time periods. When the length of each time period is one hour, the total number of the time periods is 24. The threshold value may be 12, which is half the number of the total number.

Further, when the frequency of disorder exceeds the reference frequency, determining unit 140 determines the likelihood of the mild dementia and the like to be high. The reference frequency is, for example, a frequency of five days out of one week, a frequency of 70% in a period of one week or more, a frequency of five consecutive days (that is, a frequency of 100% in a period of five days or more), or the like.

For example, when the frequency of 70% in seven days from a day one week before the examination day to a day before the examination day is defined as the reference frequency, the frequency of disorder exceeds the reference frequency on day 16 in FIG. 9. Therefore, on day 16, determining unit 140 determines the likelihood that user A is developing the mild dementia and the like to be high. Further, outputting unit 160 outputs the dementia information indicating the likelihood that user A is developing the mild dementia and the like.

By the dementia information output processing as described above, the dementia information indicating the likelihood that user A is developing the mild dementia and the like is displayed on the display of notification device 200 on the basis of the variability degree of the amount of body motion in each time period. Dementia determination devices 100b and 100c also perform operations similar to that of dementia determination device 100a, and hence the dementia information indicating the likelihood that users B and C are developing the mild dementia and the like is displayed on the display of notification device 200 installed in management office 21.

Embodiment 2

The determination of the mild dementia and the like in this embodiment is on the basis of a variation coefficient of the amount of body motion in each time period in a plurality of days. Dementia information output system 11 that is obtained by partially modifying dementia information output system 10 in Embodiment 1 is described below.

Configuration

In dementia information output system 11, dementia determination devices 100a to 100c of dementia information output system 10 described in Embodiment 1 (see FIG. 1) are modified, and the likelihood that users A to C are developing the mild dementia and the like is determined on the basis of the variation coefficient. Dementia determination device 1100a obtained by modifying dementia determination device 100a (see FIG. 2) in assisted living unit 22a in which user A lives is mainly described here.

Note that, in dementia information output system 11, dementia determination devices 100b and 100c are also modified into configurations similar to that of dementia determination device 1100a. Features of dementia information output system 11 according to this embodiment that are not illustrated here are similar to those of dementia information output system 10 described in Embodiment 1. For the same configurations, the same reference characters as those in Embodiment 1 are used and descriptions are omitted, as appropriate. In addition, the hardware elements of dementia determination device 1100a are basically the same as the hardware elements of dementia determination device 100a illustrated in FIG. 1.

Figure 10:
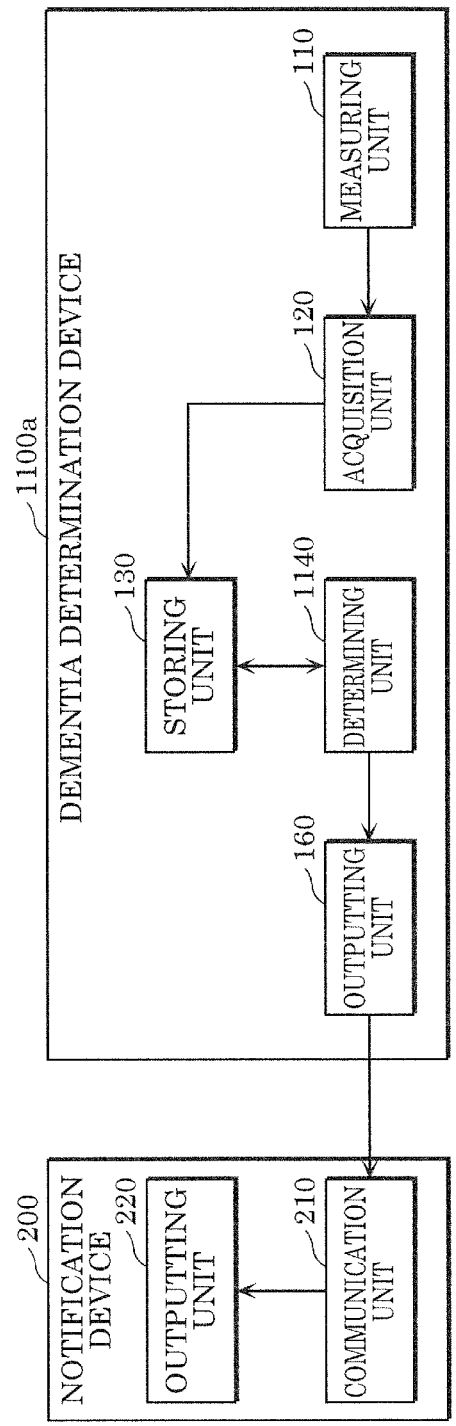
FIG. 10 is a block diagram illustrating a configuration of a dementia determination device and the like according to Embodiment 2.

FIG. 10 is a block diagram illustrating a configuration of dementia determination device 1100a in dementia information output system 11 according to this embodiment. Dementia determination device 1100a is installed in assisted living unit 22a in which user A lives. Note that, in this figure, notification device 200 installed in management office 21 is also illustrated.

Dementia determination device 1100a outputs the dementia information based on the variation coefficient of the amount of body motion in each time period in a plurality of days. Therefore, dementia determination device 1100a includes measuring unit 110, acquisition unit 120, storing unit 130, determining unit 1140, and outputting unit 160 as configuration elements as illustrated in FIG. 10.

Determining unit 1140 takes the same role as determining unit 140 described in Embodiment 1, but performs dementia determination processing that is different from that of determining unit 140. That is, determining unit 1140 determines the likelihood that user A is developing the mild dementia and the like on the basis of the variation coefficient of the amount of body motion of user A in each time period in a plurality of days.

The plurality of days herein specifically correspond to a period of two or more days. The plurality of days may correspond to one month, may correspond to one week, or may correspond to ten days. In addition, the variation coefficient is a statistic in statistics, and is a ratio of the standard deviation to the average value (that is, the standard deviation/the average value).

For example, when the length of each time period is one hour, the total number of the time periods is 24. In this case, determining unit 1140 determines the likelihood that user A is developing the mild dementia and the like on the basis of 24 variation coefficients. In addition, determining unit 1140 may determine the likelihood that user A is developing the mild dementia and the like on the basis of an average value of 24 variation coefficients and the like.

The variation coefficient of the amount of body motion of user A in each time period in a plurality of days corresponds to the degree (the variability degree) by which the amount of body motion of user A varies over the plurality of days in each of the plurality of time periods, and corresponds to the variability degree of the life pattern of user A.

Figure 11:
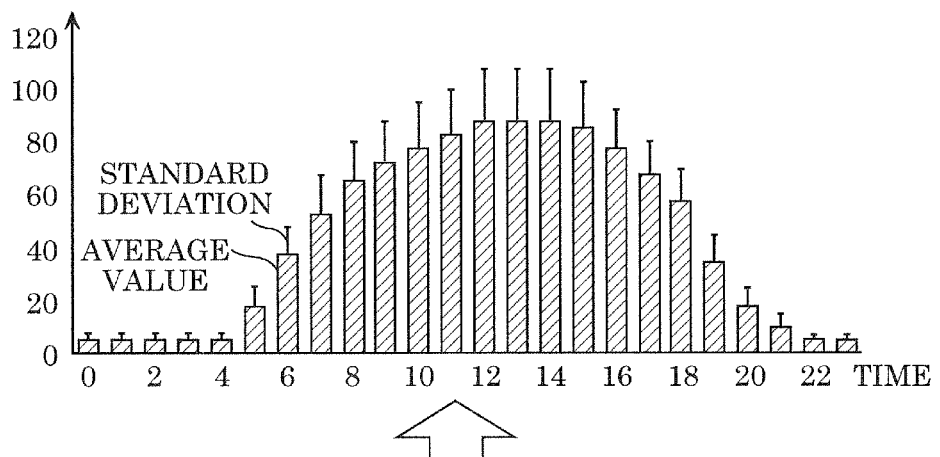
FIG. 11 is a graph indicating an average value and a standard deviation of the amount of body motion of a healthy subject in each time period in a plurality of days.
Figure 11:
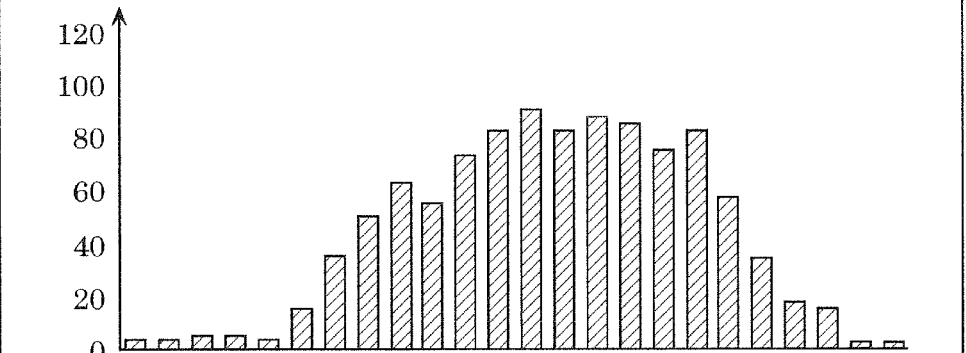
Figure 11:
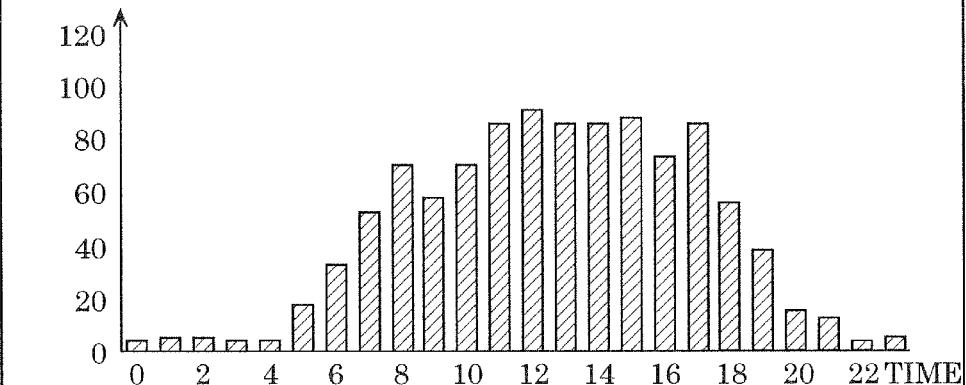
Figure 12:
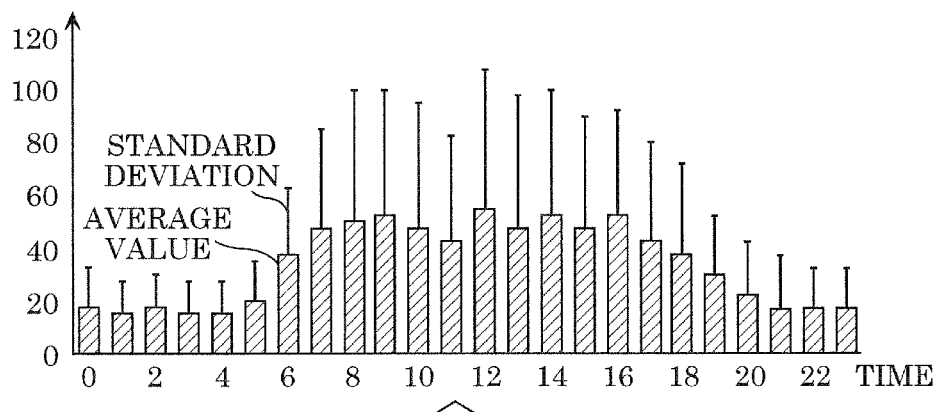
FIG. 12 is a graph indicating an average value and a standard deviation of the amount of body motion of a dementia subject in each time period in a plurality of days.
Figure 12:
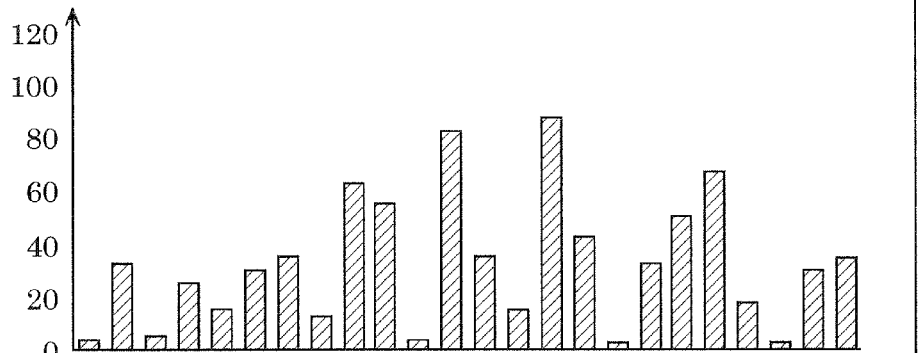
Figure 12:
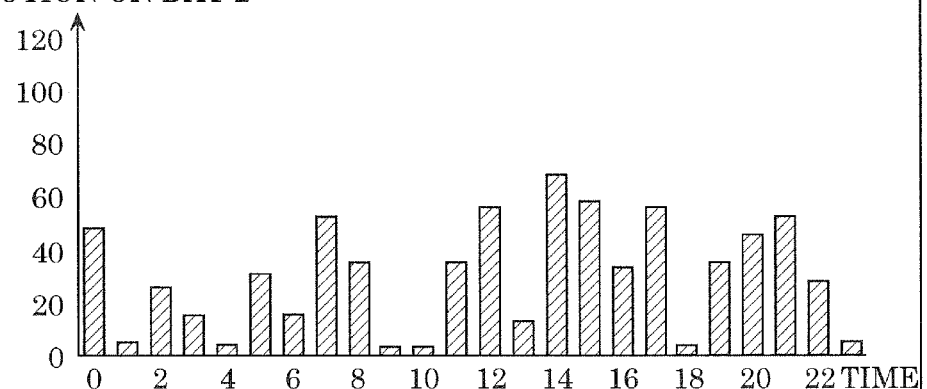

FIG. 11 and FIG. 12 are diagrams indicating the average value and the standard deviation of the amount of body motion in each time period in one month. Specifically, FIG. 11 indicates the average value and the standard deviation of the amount of body motion in one month of a healthy subject for each of the plurality of time periods, and FIG. 12 indicates the average value and the standard deviation of the amount of body motion in one month of a dementia subject for each of the plurality of time periods.

As in FIG. 11, for the healthy subject, the amount of body motion in each time period does not significantly change over the plurality of days. Therefore, in each of the plurality of time periods, the standard deviation of the amount of body motion in one month is small with respect to the average value of the amount of body motion in one month. That is, in each of the plurality of time periods, the variation coefficient of the amount of body motion in one month is small.

Meanwhile, as in FIG. 12, for the dementia subject, the amount of body motion in each time period significantly changes over the plurality of days. Therefore, in each of the plurality of time periods, the standard deviation of the amount of body motion in one month is large with respect to the average value of the amount of body motion in one month. That is, in each of the plurality of time periods, the variation coefficient of the amount of body motion in one month is large.

Therefore, determining unit 1140 determines the likelihood that the user is developing the mild dementia and the like to be higher as the variation coefficient of the amount of body motion in each time period becomes larger. In particular, determining unit 1140 may determine the likelihood that the user is developing the mild dementia and the like to be higher as an integrated variation coefficient obtained by integrating the plurality of variation coefficients of the plurality of time periods becomes larger. The integrated variation coefficient is a total value, an average value, a weighted average value, a median value, a mode value, a maximum value, a minimum value, a mid-point value, or the like of the plurality of variation coefficients of the plurality of time periods.

Operation

The operation of dementia determination device 1100a in dementia information output system 11 having the above-mentioned configuration is described below. The dementia information output processing according to this embodiment is basically the same as the dementia information output processing according to Embodiment 1 illustrated in FIG. 5, but the content of the dementia determination processing (S12 in FIG. 5) is different.

Figure 13:
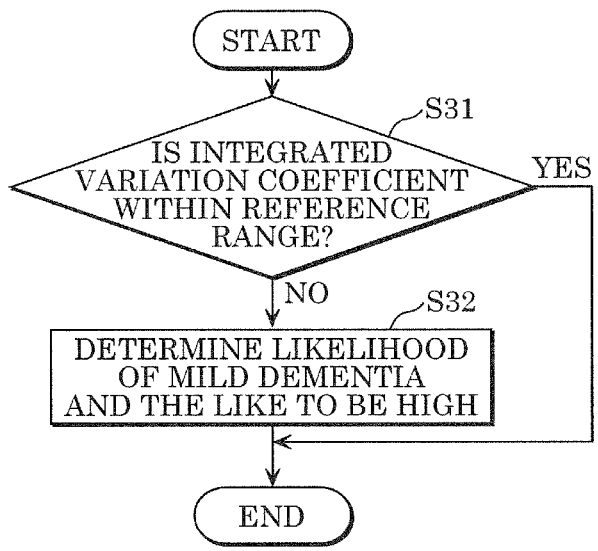
FIG. 13 is a flowchart illustrating dementia determination processing according to Embodiment 2.

FIG. 13 is a flowchart illustrating the dementia determination processing according to this embodiment. The dementia determination processing corresponds to the processing performed as the dementia determination processing (S12) illustrated in FIG. 5. The dementia determination processing is described below with reference to this figure.

Determining unit 1140 of dementia determination device 1100a acquires a plurality of variation coefficients of a plurality of time periods in an examination period, acquires an integrated variation coefficient by integrating the plurality of acquired variation coefficients, and determines whether the integrated variation coefficient is within the reference range (S31).

For example, in the acquisition of the integrated variation coefficient, determining unit 1140 may acquire an average value of the plurality of variation coefficients as the integrated variation coefficient, or may acquire a total value of the plurality of variation coefficients as the integrated variation coefficient. Each of the plurality of variation coefficients is the variation coefficient of the amount of body motion in a corresponding time period out of the plurality of time periods, and is the variation coefficient of the amount of body motion in an examination period that is two or more days. The examination period may be one week, may be one month, or may be ten days.

Further, when the integrated variation coefficient is not within the reference range (No in S31), determining unit 1140 determines the likelihood of the mild dementia and the like to be higher than when the integrated variation coefficient is within the reference range (Yes in S31) (S32). For example, determining unit 1140 determines that user A is developing the mild dementia and the like when the integrated variation coefficient is not within the reference range (No in S31), and determines that user A is not developing the mild dementia and the like when the integrated variation coefficient is within the reference range (Yes in S31).

Determining unit 1140 may reflect the determination result in storing unit 130. That is, determining unit 1140 may store the determination result of whether the integrated variation coefficient in the examination period is within the reference range in storing unit 130. In addition, determining unit 1140 may store information indicating the integrated variation coefficient in the examination period in storing unit 130. Determining unit 1140 may repeat the abovementioned processing (S31 and S32) for a plurality of examination periods.

In addition, the reference range may be defined on the basis of a plurality of reference variation coefficients that are a plurality of integrated variation coefficients in a plurality of periods (plurality of examination periods). The plurality of reference variation coefficients are a plurality of integrated variation coefficients in a plurality of periods (plurality of examination periods) preceding the examination period. The plurality of reference variation coefficients may be selected from a plurality of integrated variation coefficients in a plurality of periods (plurality of examination periods) preceding the examination period excluding one or more integrated variation coefficients determined to not be within the reference range defined for each integrated variation coefficient.

Specifically, the plurality of reference variation coefficients may be a plurality of integrated variation coefficients out of six integrated variation coefficients in six months from a month six months before the examination month to a month before the examination month excluding one or more integrated variation coefficients determined to not be within the reference range for each of the integrated variation coefficients.

Figure 14:
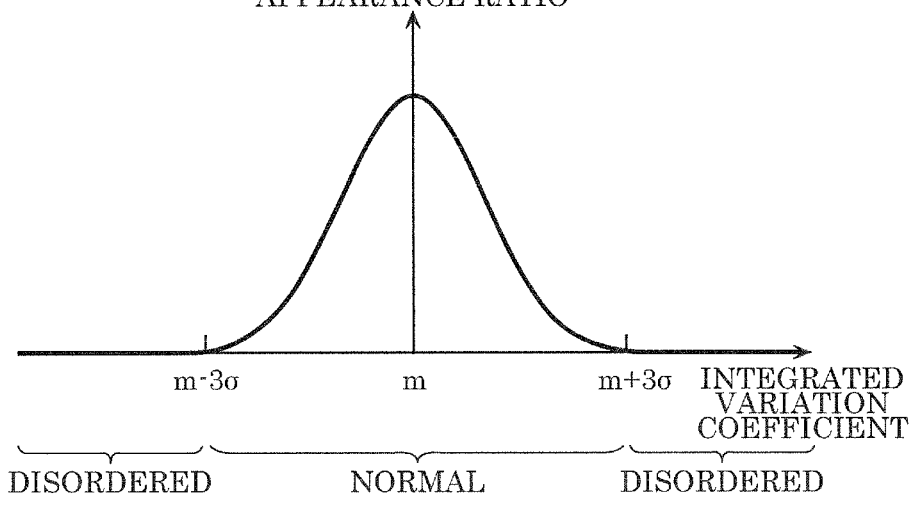
FIG. 14 is a graph for describing a reference range based on a standard deviation of an integrated variation coefficient.

FIG. 14 is a graph for describing a reference range based on a standard deviation of an integrated variation coefficient. FIG. 14 indicates the appearance ratio of the integrated variation coefficient. For example, the reference range is defined on the basis of the average value and the standard deviation of the plurality of reference variation coefficients that are the plurality of integrated variation coefficients in the plurality of periods. Note that determining unit 1140 may define (specify) the reference range.

The reference range may be defined as a range of m±3σ on the basis of an average value m and a standard deviation σ. In this case, determining unit 1140 determines the likelihood that user A is developing the mild dementia and the like by determining whether the integrated variation coefficient in the examination period is within the range of m±3σ.

The range of m±3σ is an example of a reference range based on the standard deviation. The reference range may be a range of m±σ, or may be a range of m±2σ. In addition, the reference range may be defined as a range of m±aσ with use of a satisfying a>0.

Figure 15:
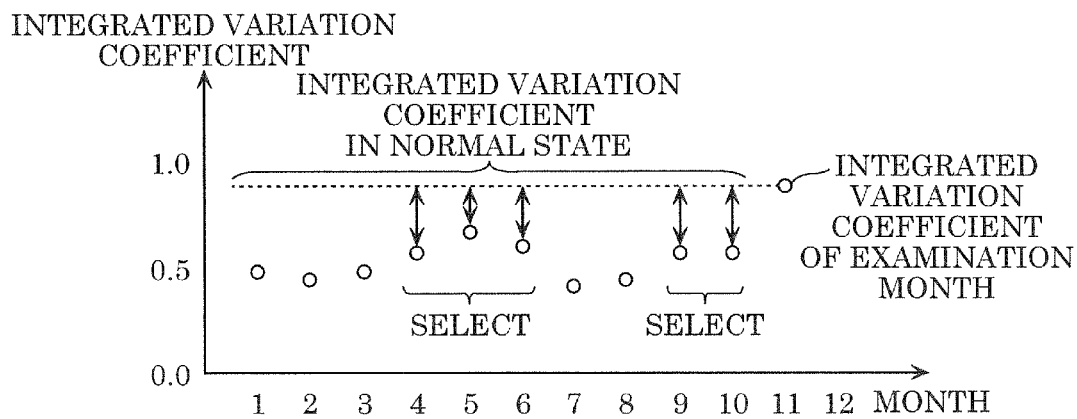
FIG. 15 is a graph for describing a reference range based on the integrated variation coefficient and a k-nearest neighbor algorithm.

FIG. 15 is a graph for describing a reference range based on the integrated variation coefficient and the k-nearest neighbor algorithm. The reference range may be defined on the basis of the k-nearest neighbor algorithm.

For example, determining unit 1140 selects a number of k reference variation coefficients from the plurality of integrated variation coefficients of the plurality of periods preceding the examination period by prioritizing the integrated variation coefficients close to the integrated variation coefficient of the examination period. Specifically, for example, determining unit 1140 selects five reference variation coefficients from ten months from a month ten months before the examination month to a month before the examination month by prioritizing the integrated variation coefficients close to the integrated variation coefficient of the examination month. At that time, the integrated variation coefficients determined in the past to not be within the reference range may be excluded from the selection.

Further, determining unit 1140 defines the reference range on the basis of an average value of the number of k selected reference variation coefficients. Specifically, determining unit 1140 defines a range of m±c as the reference range on the basis of the average value m and an allowable error c. As a result, determining unit 1140 can define the reference range, as appropriate, regardless of whether the integrated variation coefficient is in accordance with a normal distribution.

Note that the variability of the amount of body motion over the plurality of days becomes small as the variation coefficient or the integrated variation coefficient becomes small. Therefore, only the upper limit may be defined for the reference range. Alternatively, both the upper limit and the lower limit may be defined for the reference range. When the integrated variation coefficient of the examination period is lower than the lower limit of the reference range, determining unit 1140 may determine the integrated variation coefficient to be an abnormal value, and may stop the determination of the mild dementia and the like based on the integrated variation coefficient.

By the dementia information output processing as described above, the dementia information indicating the likelihood that user A is developing the mild dementia and the like is displayed on the display of notification device 200 on the basis of the variability degree of the amount of body motion in each time period. Dementia determination devices 100b and 100c also perform operations similar to that of dementia determination device 1100a, and hence the dementia information indicating the likelihood that users B and C are developing the mild dementia and the like is displayed on the display of notification device 200 installed in management office 21.

Embodiment 3

The determination of the mild dementia and the like in this embodiment is based on an intradaily variability (IV) value. The IV value corresponds not to the degree by which the amount of body motion varies over the plurality of days in each of the plurality of time periods, but to the degree by which the amount of body motion varies over a plurality of time periods. Dementia information output system 12 that is obtained by partially modifying dementia information output system 10 in Embodiment 1 is described below.

Configuration

In dementia information output system 12, dementia determination devices 100a to 100c of dementia information output system 10 described in Embodiment 1 (see FIG. 1) are modified, and the likelihood that users A to C are developing the mild dementia and the like is determined on the basis of the IV value. Dementia determination device 2100a obtained by modifying dementia determination device 100a in assisted living unit 22a in which user A lives (see FIG. 2) is mainly described here.

Note that, in dementia information output system 12, dementia determination devices 100b and 100c also are modified to a configuration similar to that of dementia determination device 2100a. Features of dementia information output system 12 according to this embodiment that are not illustrated here are similar to those of dementia information output system 10 described in Embodiment 1. For the same configurations, the same reference characters as those in Embodiment 1 are used and descriptions are omitted, as appropriate. In addition, hardware elements of dementia determination device 2100a are basically the same as the hardware elements of dementia determination device 100a illustrated in FIG. 1.

Figure 16:
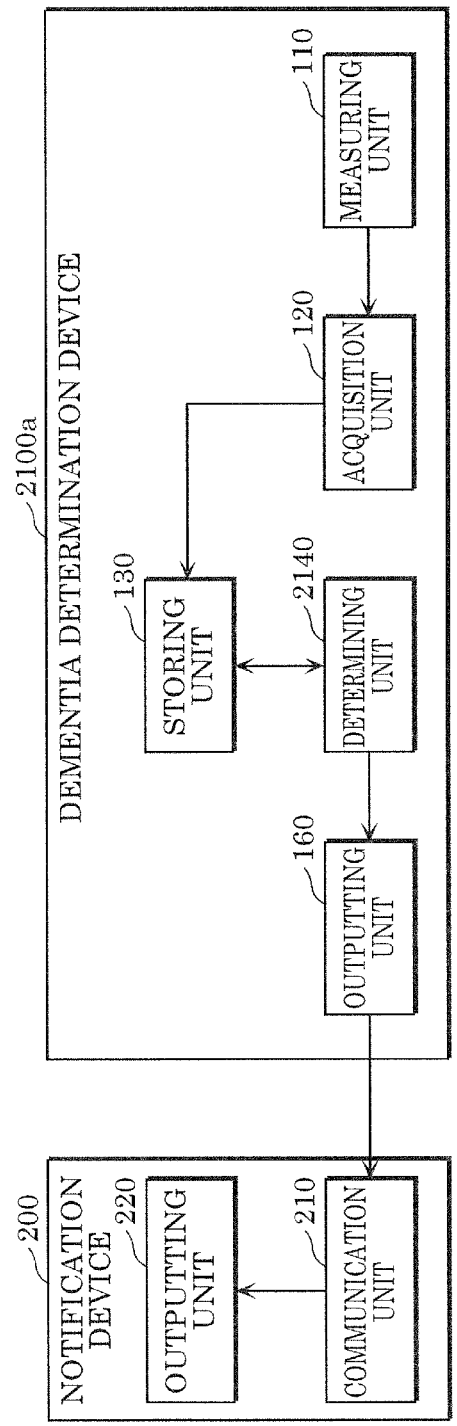
FIG. 16 is a block diagram illustrating a configuration of a dementia determination device and the like according to Embodiment 3.

FIG. 16 is a block diagram illustrating a configuration of dementia determination device 2100a in dementia information output system 12 according to this embodiment. Dementia determination device 2100a is installed in assisted living unit 22a in which user A lives. Note that, in this figure, notification device 200 installed in management office 21 is also illustrated.

Dementia determination device 2100a outputs the dementia information based on the IV value. Therefore, dementia determination device 2100a includes measuring unit 110, acquisition unit 120, storing unit 130, determining unit 2140, and outputting unit 160 as configuration elements as illustrated in FIG. 16.

Determining unit 2140 takes the same role as determining unit 140 described in Embodiment 1, but performs dementia determination processing that is different from that of determining unit 140. That is, determining unit 2140 determines the likelihood that user A is developing the mild dementia and the like on the basis of the IV value obtained from the amount of body motion of user A in a plurality of time periods.

Figure 17:
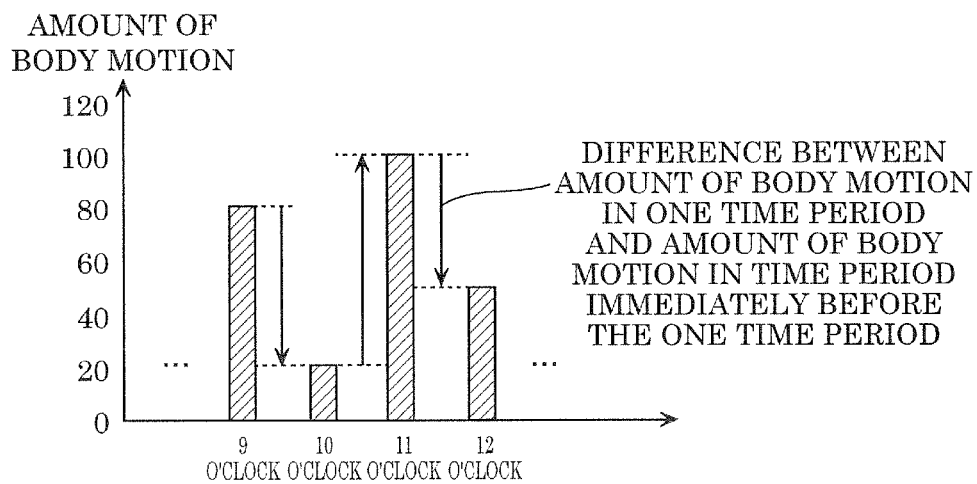
FIG. 17 is a graph for describing an IV value.

FIG. 17 is a graph for describing the IV value. The IV value is a value obtained by dividing a mean square of a difference between the amount of body motion in one time period and the amount of body motion in a time period immediately before the one time period by a variance of the amount of body motion in a plurality of time periods. That is, the IV value is expressed by the following expression.

[Expression 1]

$$IV \text{ value} = \frac{\sum_{2}^{n}(x_i - x_{i-1})^2}{\frac{n-1}{\sum_{1}^{n}(x_i - \bar{x})^2}}$$ (Expression 1)

Here, $x_i$ represents an amount of body motion in a time period i. As in FIG. 4A and FIG. 4B, for the dementia subject, the frequency of repeating sleep and awakening is high, and hence the difference between the amount of body motion in one time period and the amount of body motion in a time period immediately before the one time period is large as a whole, and the IV value is assumed to be large. Meanwhile, for the healthy subject, the difference between the amount of body motion in one time period and the amount of body motion in a time period immediately before the one time period is small as a whole as compared to the dementia subject, and hence the IV value is assumed to be small.

Therefore, determining unit 2140 determines the likelihood that user A is developing the mild dementia and the like to be higher as the IV value becomes larger.

Operation

The operation of dementia determination device 2100a in dementia information output system 12 having the above-mentioned configuration is described below. The dementia information output processing according to this embodiment is basically the same as the dementia information output processing according to Embodiment 1 illustrated in FIG. 5, but the content of the dementia determination processing (S12 in FIG. 5) is different.

Figure 18:
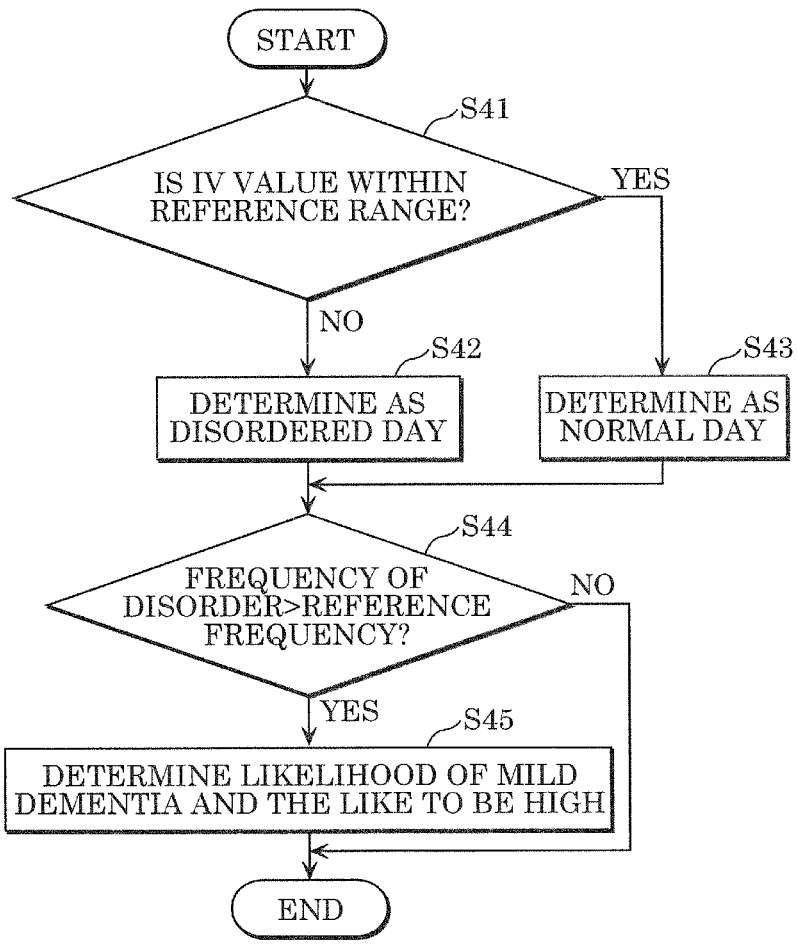
FIG. 18 is a flowchart illustrating dementia determination processing according to Embodiment 3.

FIG. 18 is a flowchart illustrating the dementia determination processing according to this embodiment. The dementia determination processing corresponds to the processing performed as the dementia determination processing (S12) illustrated in FIG. 5. The dementia determination processing is described below with reference to this figure.

Determining unit 2140 of dementia determination device 2100a acquires the IV value on the basis of the amount of body motion on the examination day, and determines whether the IV value is within the reference range (S41). Further, determining unit 2140 determines the examination day to be a disordered day when the IV value based on the amount of body motion on the examination day is not within the reference range (No in S41) (S42). Meanwhile, determining unit 2140 determines the examination day to be a normal day when the IV value based on the amount of body motion on the examination day is within the reference range (Yes in S41) (S43).

Determining unit 2140 may reflect the determination result in storing unit 130. That is, determining unit 2140 may store the determination result of whether the examination day is a disordered day in storing unit 130. In addition, the IV value may be stored in storing unit 130. Determining unit 2140 repeats the abovementioned processing (S41 to S43) for a plurality of examination days.

Next, determining unit 2140 determines whether the frequency of disorder that is the occurrence frequency of the disordered day is higher than the reference frequency (S44). Further, when the frequency of disorder is higher than the reference frequency (Yes in S44), determining unit 2140 determines the likelihood of the mild dementia and the like to be higher than when the frequency of disorder is not higher than the reference frequency (No in S44) (S45).

For example, determining unit 2140 determines that user A is developing the mild dementia and the like when the frequency of disorder is higher than the reference frequency (Yes in S44), and determines that user A is not developing the mild dementia and the like when the frequency of disorder is not higher than the reference frequency (No in S44).

The reference range (the reference range in S41) for determining whether the IV value is within the reference range is defined on the basis of the IV value in a plurality of reference days. The plurality of reference days are a plurality of days preceding the examination day. The plurality of reference days may be selected from a plurality of days preceding the examination day excluding the days determined to be the disordered day. More specifically, the plurality of reference days may be a plurality of days out of a plurality of days from a day one month before the examination day to a day before the examination day excluding the days determined to be the disordered day.

For example, the reference range is defined on the basis of the average value and the standard deviation of a plurality of IV values in a plurality of reference days. Note that determining unit 2140 may define (specify) the reference range. In addition, whether the IV value is within the reference range corresponds to whether a standard score (standardized score) of the IV value is within a predetermined range. The standard score of the IV value is herein a value obtained by (the IV value−the average value)/the standard deviation.

Figure 19:
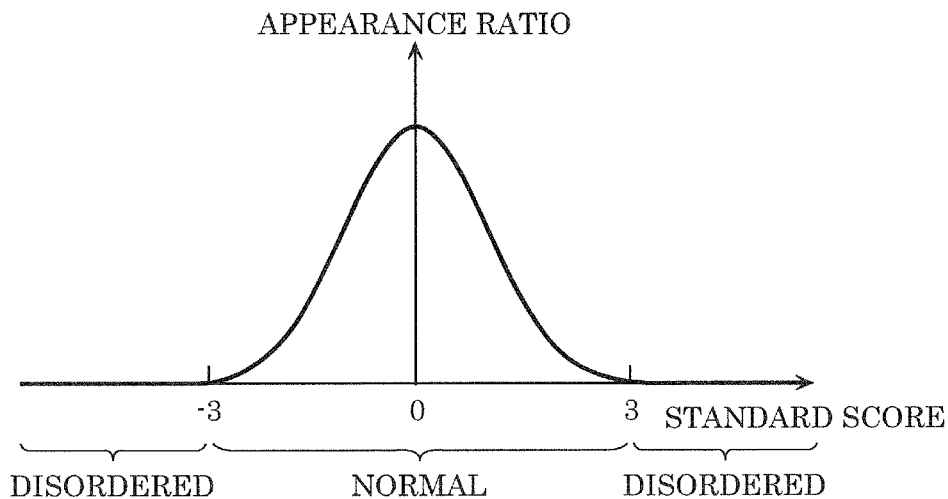
FIG. 19 is a graph for describing a reference range based on a standard deviation of the IV value.

FIG. 19 is a graph for describing the reference range based on the standard deviation of the IV value. FIG. 19 indicates the appearance ratio of the standard score of the IV value in the plurality of reference days.

The reference range may be defined as a range of $m \pm 3\sigma$ on the basis of an average value m and a standard deviation $\sigma$ of a plurality of IV values in a plurality of reference days. The range of $m \pm 3\sigma$ with respect to the IV value corresponds to the range of ±3 with respect to the standard score of the IV value. Further, determining unit 2140 may determine whether the examination day is a disordered day by determining whether the IV value on the examination day is within the range of $m \pm 3\sigma$ by determining whether the standard score of the IV value on the examination day is within the range of ±3.

The range of ±3 is an example of a range with respect to the standard score of the IV value. The range with respect to the standard score of the IV value may be a range of ±1, or may be a range of ±2. In addition, the range with respect to the standard score of the IV value may be defined as a range of ±a with use of a satisfying a>0.

Similarly, the range of $m \pm 3\sigma$ is an example of a reference range with respect to an IV value. The reference range with respect to the IV value may be a range of $m \pm \sigma$, or may be a range of $m \pm 2\sigma$. In addition, the reference range with respect to the IV value may be defined as a range of $m \pm a\sigma$ with use of a satisfying a>0.

Figure 20:
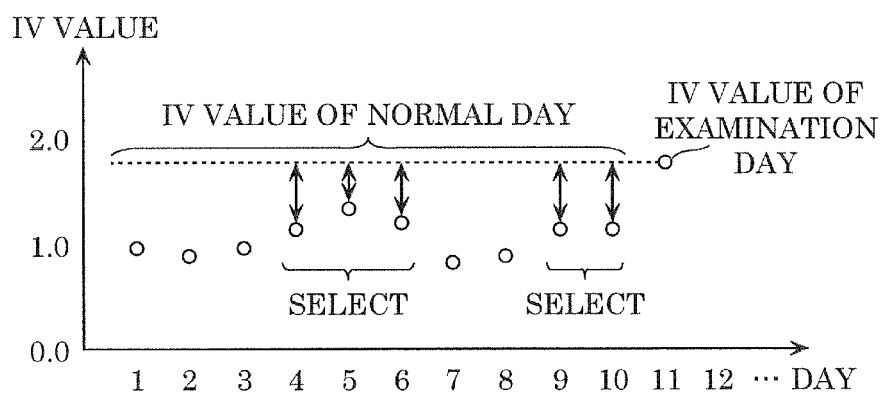
FIG. 20 is a graph for describing a reference range based on the IV value and a k-nearest neighbor algorithm.

FIG. 20 is a graph for describing a reference range based on the IV value and the k-nearest neighbor algorithm. The reference range may be defined on the basis of the k-nearest neighbor algorithm.

For example, determining unit 2140 selects a number of k reference days from a plurality of days preceding the examination day by prioritizing days of which IV values are close to that of the examination day. Specifically, for example, determining unit 2140 selects five reference days from ten days from a day ten days before the examination day to a day before the examination day by prioritizing days of which IV values are close to that of the examination day. The day determined to be the disordered day may be excluded from the selection.

Further, determining unit 2140 defines the reference range on the basis of an average value of the IV values of the number of k selected reference days. Specifically, determining unit 2140 defines a range of m±c as the reference range on the basis of an average value m and an allowable error c. As a result, determining unit 2140 can define the reference range, as appropriate, regardless of whether the IV value is in accordance with a normal distribution.

Figure 21:
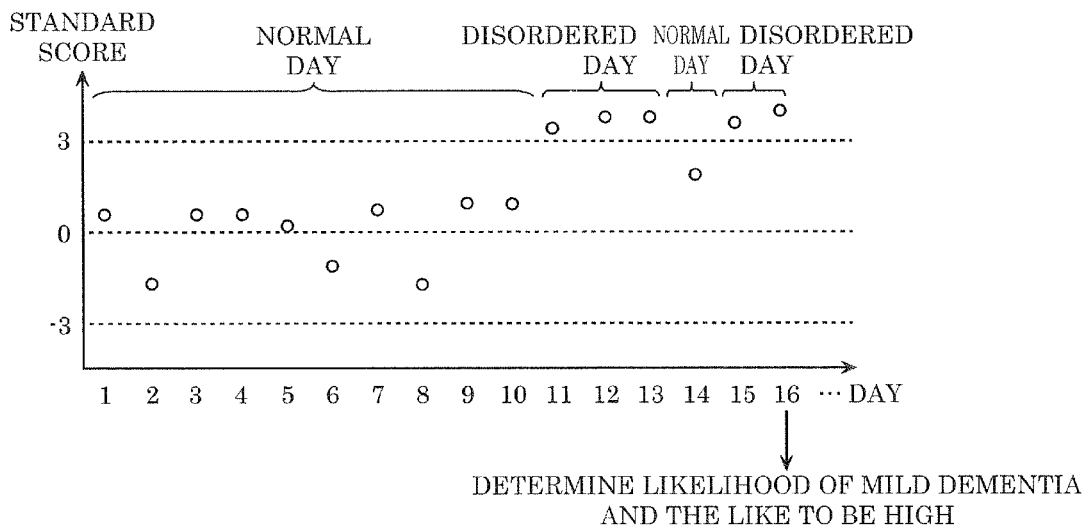
FIG. 21 is a schematic view illustrating the frequency of disorder based on the IV value.

FIG. 21 is a schematic view illustrating the frequency of disorder based on the IV value. Determining unit 2140 determines the examination day to be a disordered day when the IV value on the examination day is not within the reference range for each of the plurality of examination days. In the example in FIG. 21, when the standard score of the IV value on the examination day is not within a predetermined range (a range of ±3), determining unit 2140 determines that the IV value on the examination day is not within the reference range, and determines the examination day to be a disordered day.

Note that determining unit 2140 may determine whether the examination day is a disordered day in accordance with whether the IV value on the examination day is within the reference range based on the standard deviation, or may determine whether the examination day is a disordered day in accordance with whether the IV value on the examination day is within the reference range based on the k-nearest neighbor algorithm.

Further, determining unit 2140 determines the likelihood of the mild dementia and the like to be high when the frequency of disorder exceeds the reference frequency. The reference frequency is, for example, a frequency of five days out of one week, a frequency of 70% in a period of one week or more, a frequency of five consecutive days (that is, a frequency of 100% in a period of five days or more), or the like.

For example, when the frequency of 70% in seven days from a day one week before the examination day to a day before the examination day is defined as the reference frequency, the frequency of disorder exceeds the reference frequency on day 16 in FIG. 21. Therefore, on day 16, determining unit 2140 determines the likelihood that user A is developing the mild dementia and the like to be high. Further, outputting unit 160 outputs the dementia information indicating the likelihood that user A is developing the mild dementia and the like.

Figure 22:
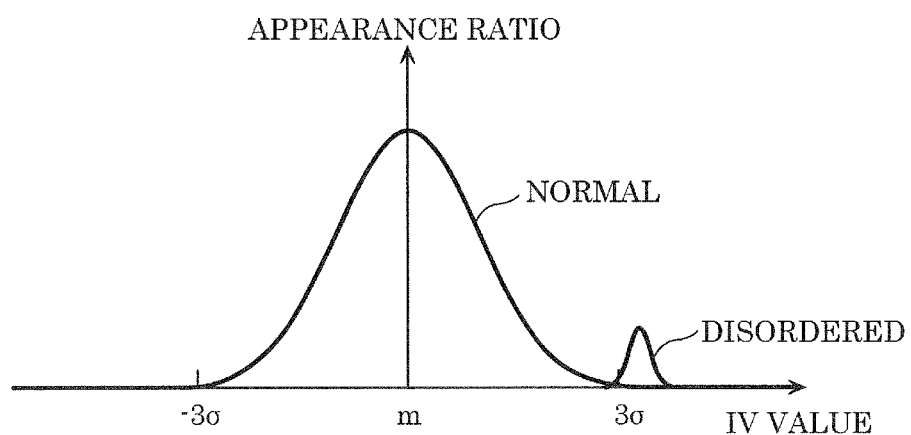
FIG. 22 is a graph indicating the appearance ratio of the IV value on a normal day and the appearance ratio of the IV value on a disordered day.

FIG. 22 is a graph indicating the appearance ratio of the IV value on a normal day and the appearance ratio of the IV value on a disordered day. The appearance ratio of the IV value on a normal day and the appearance ratio of the IV value on a disordered day are expressed as in FIG. 22 when the appearance ratios are in accordance with normal distributions. That is, the average value, the standard deviation, and the like of the IV value on a normal day are different from the average value, the standard deviation, and the like of the IV value on a disordered day. Determining unit 2140 may accumulate information on the IV value on a normal day and information on the IV value on a disordered day in storing unit 130.

Note that the repeating of sleep and awakening decreases as the IV value (or the standard score of the IV value) decreases. Therefore, only the upper limit may be defined for the reference range. Alternatively, both the upper limit and the lower limit may be defined for the reference range. When the IV value is lower than the lower limit of the reference range, determining unit 2140 may determine the IV value to be an abnormal value and may stop the determination of the mild dementia and the like. In addition, in this case, the examination day may be handled in a way similar to the disordered day and not as a normal day.

By the dementia information output processing as described above, the dementia information indicating the likelihood that user A is developing the mild dementia and the like is displayed on the display of notification device 200 on the basis of the degree by which the amount of body motion varies over the plurality of time periods. Dementia determination devices 100*b* and 100*c* also perform operations similar to that of dementia determination device 2100*a*, and hence the dementia information indicating the likelihood that users B and C are developing the mild dementia and the like is displayed on the display of notification device 200 installed in management office 21.

Other Embodiments and the Like

Dementia information output systems 10, 11, and 12 have been described above on the basis of Embodiments 1, 2, and 3, but Embodiments 1, 2, and 3, and dementia information output systems 10, 11, and 12 are merely examples, and various modifications, additions, omissions, and the like can be made.

For example, in Embodiments 1, 2, and 3, dementia information output systems 10, 11, and 12 are used in nursing care facility 20. However, dementia information output systems 10, 11, and 12 may be used in a house (such as independent housing or an individual dwelling unit in a housing complex), an elderly housing complex, a hospital, or other facilities.

In addition, dementia determination devices 100*a*, 1100*a*, and 2100*a* in dementia information output systems 10, 11, and 12 may include presentation device (display device) such as a display.

Figure 23:
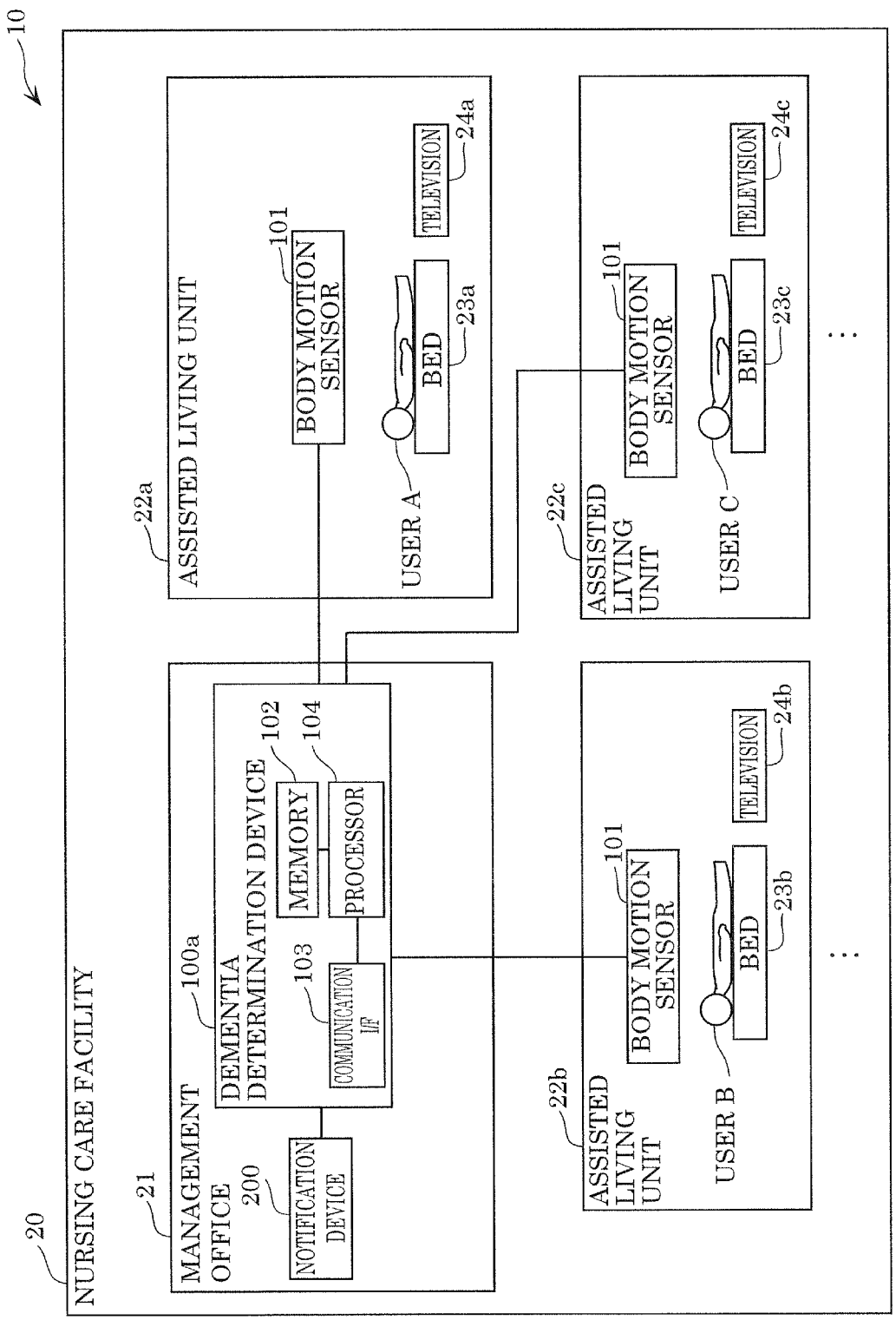
FIG. 23 is a schematic configuration view illustrating an example of a configuration of a dementia information output system according to another embodiment.

In addition, dementia determination device 100*a* may be installed in management office 21 except for body motion sensor 101. Further, dementia determination device 100*a* may determine the mild dementia and the like on the basis of the amount of body motion by acquiring the amount of body motion of users A to C from body motion sensor 101 installed in assisted living units 22*a* to 22*c* and output the dementia information on users A to C. In this case, dementia determination devices 100*b* and 100*c* do not necessarily need to be installed except for body motion sensor 101. FIG. 23 illustrates a configuration example of a case where dementia determination device 100*a* is installed in management office 21.

In addition, dementia information output system 10, 11, or 12 only needs to include one dementia determination device 100*a*, 1100*a*, or 2100*a* when the determination of the mild dementia and the like is performed for only one user A.

In addition, the transmission destination of the dementia information is not limited to notification device 200 installed in management office 21. For each of dementia determination devices 100*a*, 1100*a*, and 2100*a*, communication I/F 103 may be connectable, for example, to a wide area network such as a telephone network or the Internet. Further, notification device 200 may be a communication device and the like (specifically, a personal computer and the like) installed in a location different from management office 21, or an information communication terminal and the like (specifically, a smartphone and the like) that are mobile objects.

For example, it is useful if dementia determination device 100*a* is installed in a house of an elderly person living alone and an e-mail address, etc., of a smartphone of a family member living away from the elderly person is stored into dementia determination device 100*a* so that outputting unit 160 outputs the dementia information to the smartphone. Furthermore, dementia determination devices 100*a*, 1100*a*, and 2100*a* may transmit the dementia information to two or more destinations.

In addition, in Embodiments 1, 2, and 3, dementia determination devices 100*a*, 1100*a*, and 2100*a* include body motion sensor 101. However, dementia determination devices 100*a*, 1100*a*, and 2100*a* do not necessarily need to include body motion sensor 101, and may acquire the amount of body motion from external body motion sensor 101. In addition, dementia determination devices 100*a*, 1100*a*, and 2100*a* may acquire the amount of body motion from information recorded on a recording medium. In the case as above, dementia determination devices 100*a*, 1100*a*, and 2100*a* do not necessarily need to include measuring unit 110.

In addition, in a configuration in which dementia determination device 100*a*, 1100*a*, or 2100*a* and body motion sensor 101 are separated from each other, measuring unit 110 and acquisition unit 120 may be included in body motion sensor 101.

In addition, the division of roles of the configuration elements in dementia determination device 100*a*, 1100*a*, or 2100*a* is merely an example, and acquisition unit 120 may include measuring unit 110, or outputting unit 160 may include determining unit 140, 1140, or 2140.

In addition, storing unit 130 may be included in acquisition unit 120, or may be included in determining unit 140, 1140, or 2140. Dementia determination devices 100*a*, 1100*a*, and 2100*a* do not necessarily need to include storing unit 130, and may use external storing unit 130. In addition, the amount of body motion acquired by acquisition unit 120 may be directly used in determining unit 140, 1140, or 2140 without passing through storing unit 130. In this case, dementia determination devices 100*a*, 1100*a*, and 2100*a* do not necessarily need to include storing unit 130.

In addition, acquisition unit 120 may acquire the amount of body motion without accumulating the amount of body motion for each time period, and determining unit 140, 1140, or 2140 may accumulate the amount of body motion acquired by acquisition unit 120 for each time period and acquire the amount of body motion accumulated in each time period.

In addition, in Embodiments 1 and 3, an operation of determining the likelihood that user A is developing the mild dementia and the like to be high when the frequency of disorder is higher than the reference frequency is described. The operation is an example of an operation of determining the likelihood that user A is developing the mild dementia and the like on the basis of the frequency of disorder, and is an example of an operation of determining the likelihood that user A is developing the mild dementia and the like to be higher as the frequency of disorder becomes higher.

In addition, in Embodiment 2, an operation of determining the likelihood that user A is developing the mild dementia and the like to be high when the integrated variation coefficient is not within the reference range is described. The operation is an example of an operation of determining the likelihood that user A is developing the mild dementia and the like on the basis of the variation coefficient in each of the plurality of time periods. For example, determining unit 1140 may determine the likelihood that user A is developing the mild dementia and the like to be higher as the variation coefficient (or the integrated variation coefficient) in each of the plurality of time periods becomes higher.

In addition, determining unit 140, 1140, or 2140 may determine whether user A is developing the mild dementia and the like or may determine the degree of the likelihood that user A is developing the mild dementia and the like upon determining the likelihood that user A is developing the mild dementia and the like. Further, the dementia information indicating the likelihood that user A is developing the mild dementia and the like may indicate whether user A is developing the mild dementia and the like, or may indicate the degree of the likelihood that user A is developing the mild dementia and the like with use of percentage.

In addition, determining unit 140, 1140, or 2140 may determine the likelihood that user A is developing the mild dementia and the like to be higher in stages as the frequency of disorder or the variation coefficient becomes higher on the basis of one or more threshold values. Alternatively, determining unit 140, 1140, or 2140 may determine the likelihood that user A is developing the mild dementia and the like to be higher in a continuous manner without stages as the frequency of disorder or the variation coefficient becomes higher regardless of the threshold value.

In other words, determining unit 140, 1140, or 2140 may increase the likelihood of the mild dementia and the like in stages or increase the likelihood of the mild dementia and the like in a continuous manner as the frequency of disorder or the variation coefficient becomes higher.

In addition, Embodiments 1, 2, and 3 can be combined. That is, determining units 140, 1140, and 2140 may be combined. A determining unit obtained by combining determining units 140, 1140, and 2140 may perform the three dementia determination processing in Embodiments 1, 2, and 3, and may eventually determine the likelihood that user A is developing the mild dementia and the like on the basis of the three determination results. The determining unit may average the three determination results, or may weight and average the three determination results.

In addition, Embodiments 1, 2, and 3 have described that outputting unit 160 may display the dementia information on the display, but the dementia information may be presented in a method other than displaying. Examples of the presentation method other than displaying include a method of reproducing the dementia information from a speaker and the like in a form of speech, for example.

In addition, the execution order of the processing in dementia determination devices 100a, 1100a, 2100a, and the like is not limited to the execution order illustrated in FIG. 5, FIG. 6, FIG. 13, FIG. 18, or the like. The execution order may be changed, or a part of the processing may be omitted.

In addition, all or a part of the processing illustrated in FIG. 5, FIG. 6, FIG. 13, FIG. 18, or the like may be executed by software.

For example, all or a part of the processing is executed when processor 104 of dementia determination device 100a, 1100a, 2100a, or the like executes a control program stored in memory 102. In addition, the control program may be recorded on a non-temporary recording medium such as a CD-ROM, and may be distributed.

Further, the distributed control program may be installed in a computer, and may be executed by a microprocessor and the like of the computer. As a result, the computer can be operated as dementia determination device 100a, 1100a, 2100a, or the like, and all or a part of the processing illustrated in FIG. 5, FIG. 6, FIG. 13, or FIG. 18 can be executed by the computer.

In addition, dementia determination devices 100a, 1100a, and 2100a may include the elements illustrated in FIG. 2, FIG. 9, and FIG. 16 as hardware elements. For example, dementia determination devices 100a, 1100a, and 2100a may include the elements illustrated in FIG. 2, FIG. 9, and FIG. 16 as dedicated or general-purpose circuits.

Furthermore, forms realized by arbitrarily combining the configurations and operations described in the above embodiments are included within the scope of the present invention. Note that various general or specific aspects of the present invention include one or a combination of, for example, device, system, and method. The configuration, modified aspect, advantageous effect, etc., of the dementia information output system according to an aspect of the present invention are described below.

(1) Dementia information output system 10 (or 11) according to an aspect of the present invention includes acquisition unit 120, determining unit 140 (or 1140), and outputting unit 160 (or 220).

Acquisition unit 120 acquires the amount of body motion of user A. Determining unit 140 (or 1140) determines the likelihood that user A is developing the mild dementia and the like on the basis of the variability degree that is the degree by which the amount of body motion varies over the plurality of days in each of the plurality of time periods. Outputting unit 160 (or 220) outputs the dementia information indicating the likelihood determined by determining unit 140 (or 1140).

As a result, dementia information output system 10 (or 11) can determine the likelihood of the mild dementia and the like on the basis of the variability degree relating to the amount of body motion even when additional work is not performed with respect to the daily work. The variability degree is a degree by which the amount of body motion varies over the plurality of days in each of the plurality of time periods, and corresponds to the variability degree (instability degree) of the life pattern over the plurality of days.

Therefore, dementia information output system 10 (or 11) can determine the likelihood of the mild dementia and the like, as appropriate, on the basis of the variability degree of the life pattern over the plurality of days.

(2) For example, determining unit 140 may determine the likelihood that user A is developing the mild dementia and the like on the basis of the occurrence frequency of the disordered day that is a day in which the number of the time periods in which the amount of body motion is not within the reference range is larger than the threshold value. In addition, the reference range may be defined on the basis of the amount of body motion in the plurality of reference days.

As a result, dementia information output system 10 can determine the likelihood of the mild dementia and the like on the basis of the occurrence frequency of the disordered day in which the pattern of the amount of body motion is deviated as compared to the reference range based on the plurality of reference days.

(3) For example, determining unit 140 may determine the likelihood that user A is developing the mild dementia and the like to be higher as the occurrence frequency of the disordered day becomes higher.

As a result, dementia information output system 10 can determine the likelihood that user A is developing the mild dementia and the like to be relatively high when the occurrence frequency of the disordered day is high as compared to when the occurrence frequency of the disordered day is low. Therefore, determining unit 140 can determine the likelihood that user A is developing the mild dementia and the like in a more appropriate manner.

(4) For example, determining unit 140 may acquire, for each of the plurality of examination days, the occurrence frequency of the disordered day by determining whether the examination day is a disordered day, and may determine the likelihood that user A is developing the mild dementia and the like on the basis of the acquired occurrence frequency.

In addition, the reference range for determining whether the examination day is a disordered day may be defined for each of the plurality of time periods on the basis of the average value and the standard deviation of the amount of body motion in the time period in the plurality of reference days. In addition, the plurality of reference days may be selected from the plurality of days preceding the examination day excluding one or more days determined to be the disordered day.

As a result, the reference range is defined on the basis of the average value and the standard deviation of the amount of body motion in the plurality of reference days that are not the disordered days. Therefore, dementia information output system 10 can determine the likelihood that user A is developing the mild dementia and the like by determining whether the examination day is a disordered day on the basis of the appropriate reference range.

(5) For example, determining unit 140 may acquire, for each of the plurality of examination days, the occurrence frequency of the disordered day by determining whether the examination day is a disordered day, and may determine the likelihood that user A is developing the mild dementia and the like on the basis of the acquired occurrence frequency.

In addition, the reference range for determining whether the examination day is the disordered day may be defined for each of the plurality of time periods on the basis of the average value of the amount of body motion in the time period in the plurality of reference days. In addition, the plurality of reference days may be selected for each of the plurality of time periods from the plurality of days preceding the examination day excluding one or more days determined to be the disordered day in such a manner that the plurality of reference days are selected in order of closeness to the amount of body motion in the time period on the examination day, starting with a closest day first.

As a result, the reference range is defined on the basis of the average value of the amount of body motion in the plurality of reference days of which the amount of body motion is close to that of the examination day and which are not the disordered day. Therefore, dementia information output system 10 can determine the likelihood that user A is developing the mild dementia and the like by determining whether the examination day is a disordered day on the basis of the appropriate reference range.

(6) For example, determining unit 1140 may determine the likelihood that user A is developing the mild dementia and the like on the basis of the variation coefficient defined for each of the plurality of time periods. Specifically, the variation coefficient is defined, for each of the plurality of time periods, as the ratio of the standard deviation of the amount of body motion in the time period in the plurality of days to the average value of the amount of body motion in the time period in the plurality of days.

As a result, dementia information output system 11 can determine the likelihood of the mild dementia and the like on the basis of the variation coefficient in each of the plurality of time periods. The variation coefficient expresses the degree by which the amount of body motion varies over the plurality of days in each of the plurality of time periods. Therefore, dementia information output system 11 can determine the likelihood that user A is developing the mild dementia and the like on the basis of an appropriate index value of the variability degree.

(7) For example, determining unit 1140 may determine the likelihood that user A is developing the mild dementia and the like to be higher as the variation coefficient in each of the plurality of time periods becomes higher.

As a result, dementia information output system 11 can determine the likelihood that user A is developing the mild dementia and the like to be relatively high when the variation coefficient is high as compared to when the variation coefficient is low. Therefore, determining unit 1140 can determine the likelihood that user A is developing the mild dementia and the like in a more appropriate manner.

(8) For example, determining unit 1140 may acquire, for each of the plurality of examination periods that each are a period of two or more days, the plurality of variation coefficients, and may acquire the integrated variation coefficient by integrating the plurality of acquired variation coefficients. The plurality of variation coefficients are the plurality of variation coefficients of the plurality of time periods in the examination period, and each of the plurality of variation coefficients is the variation coefficient of the corresponding time period out of the plurality of time periods.

Further, determining unit 1140 may determine whether the integrated variation coefficient of the examination period is within the reference range defined with respect to the integrated variation coefficient of the examination period. Further, determining unit 1140 may determine the likelihood that user A is developing the mild dementia and the like to be high when it is determined that the integrated variation coefficient of the examination period is not within the reference range defined with respect to the integrated variation coefficient of the examination period than when the integrated variation coefficient of the examination period is determined to be within the reference range.

In addition, the reference range defined with respect to the integrated variation coefficient of the examination period may be defined on the basis of the average value and the standard deviation of the plurality of reference variation coefficients. In addition, the plurality of reference variation coefficients may be selected from the plurality of integrated variation coefficients of the plurality of examination periods preceding the examination period excluding one or more integrated variation coefficients determined to not be within the reference range defined for each of the one or more integrated variation coefficients.

As a result, dementia information output system 11 can determine the likelihood that user A is developing the mild dementia and the like, as appropriate, on the basis of the reference range defined on the basis of the average value and the standard deviation of the plurality of reference variation coefficients that are appropriate, and the integrated variation coefficient of the examination period.

(9) For example, determining unit 1140 may acquire, for each of the plurality of examination periods that each are a period of two or more days, the plurality of variation coefficients, and may acquire the integrated variation coefficient by integrating the plurality of acquired variation coefficients. The plurality of variation coefficients are the plurality of variation coefficients of the plurality of time periods in the examination period, and each of the plurality of variation coefficients is the variation coefficient of the corresponding time period out of the plurality of time periods.

Further, determining unit 1140 may determine whether the integrated variation coefficient of the examination period is within the reference range defined with respect to the integrated variation coefficient of the examination period. Further, determining unit 1140 may determine the likelihood that user A is developing the mild dementia and the like to be high when it is determined that the integrated variation coefficient of the examination period is not within the reference range defined with respect to the integrated variation coefficient of the examination period than when the integrated variation coefficient of the examination period is determined to be within the reference range.

In addition, the reference range defined with respect to the integrated variation coefficient of the examination period may be defined on the basis of the average value of the plurality of reference variation coefficients. In addition, the plurality of reference variation coefficients may be selected from the plurality of integrated variation coefficients of the plurality of examination periods preceding the examination period excluding one or more integrated variation coefficients determined to not be within the reference range defined for each of the one or more integrated variation coefficients in such a manner that the plurality of reference variation coefficients are selected in order of closeness to the integrated variation coefficient of the examination period.

As a result, dementia information output system 11 can determine the likelihood that user A is developing the mild dementia and the like, as appropriate, on the basis of the reference range defined on the basis of the average value of the plurality of reference variation coefficients that are appropriate, and the integrated variation coefficient of the examination period.

(10) For example, outputting unit 160 (or 220) may output the dementia information by presenting the dementia information. As a result, dementia information output system 10 (or 11) can directly perform notification of the dementia information.

(11) For example, outputting unit 160 may output the dementia information by transmitting the dementia information to notification device 200. As a result, dementia information output system 10 (or 11) can perform notification of the dementia information via notification device 200.

(12) The control program according to an aspect of the present invention is a control program for causing an apparatus including microprocessor 104 (dementia determination device 100*a*, 1100*a*, or the like) to execute the dementia information output processing.

The dementia information output processing includes an acquisition step (S11), a determination step (S12), and an output step (S13). In the acquisition step (S11), the amount of body motion of user A is acquired. In the determination step (S12), the likelihood that user A is developing the mild dementia and the like is determined on the basis of the variability degree that is the degree by which the amount of body motion varies over the plurality of days in each of the plurality of time periods. In the output step (S13), the dementia information indicating the likelihood determined in the determination step (S12) is output.

As a result, the apparatus (dementia determination device 100*a*, 1100*a*, or the like) that executes the control program can determine the likelihood of the mild dementia and the like, as appropriate.

The invention claimed is:

1. A dementia information output apparatus, comprising:
an acquisition circuit that acquires an amount of body motion of a user;
a determining circuit that determines a likelihood that the user is developing a mild dementia on a basis of a variability degree, wherein the variability degree indicates a degree by which the amount of body motion varies in each time period of a plurality of time periods of a day over a plurality of days, respectively; and
an outputting circuit that outputs dementia information indicating the likelihood determined by the determining circuit, wherein:
a timing and a duration of each of the plurality of time periods are common to each of the plurality of days,
the variability degree is determined for each time period of the plurality of time periods over the plurality of days,
the variability degree in each time period of the plurality of time periods corresponds to whether the amount of body motion in the time period of each of the plurality of days is within or not within a reference range defined on a basis of the amount of body motion in the time period in a plurality of reference days,
the determining circuit determines one or more disordered days, each of which is a day in which a number of time periods in which the amount of body motion is not within the reference range is larger than a threshold value,
the determining circuit determines the likelihood on a basis of an occurrence frequency of the one or more disordered days,
the determining circuit acquires the occurrence frequency of the one or more disordered days by determining, for each of a plurality of examination days, whether an examination day is a disordered day, and determines the likelihood on a basis of the acquired occurrence frequency, and
the reference range for determining whether the examination day is the disordered day is defined for each of the plurality of time periods on a basis of an average value and a standard deviation of the amount of body motion in the time period in the plurality of reference days selected from a plurality of days preceding the examination day excluding one or more days determined to be the disordered day.

2. The dementia information output apparatus according to claim 1, wherein
the determining circuit determines the likelihood to be higher as the occurrence frequency becomes higher.

3. The dementia information output apparatus according to claim 1, wherein
the outputting circuit outputs the dementia information by presenting the dementia information.

4. The dementia information output apparatus according to claim 1, wherein
the outputting circuit outputs the dementia information by transmitting the dementia information to a notification device.

5. A dementia information output apparatus, comprising:
an acquisition circuit that acquires an amount of body motion of a user;
a determining circuit that determines a likelihood that the user is developing a mild dementia on a basis of a variability degree, wherein the variability degree indicates a degree by which the amount of body motion varies in each time period of a plurality of time periods of a day over a plurality of days, respectively; and
an outputting circuit that outputs dementia information indicating the likelihood determined by the determining circuit, wherein:
a timing and a duration of each of the plurality of time periods are common to each of the plurality of days,
the variability degree is determined for each time period of the plurality of time periods over the plurality of days,
the variability degree in each time period of the plurality of time periods corresponds to whether the amount of body motion in the time period of each of the plurality of days is within or not within a reference range defined on a basis of the amount of body motion in the time period in a plurality of reference days,
the determining circuit determines one or more disordered days, each of which is a day in which a number of time periods in which the amount of body motion is not within the reference range is larger than a threshold value,
the determining circuit determines the likelihood on a basis of an occurrence frequency of the one or more disordered days,
the determining circuit acquires the occurrence frequency of the one or more disordered days by determining, for each of a plurality of examination days, whether an examination day is a disordered day, and determines the likelihood on a basis of the acquired occurrence frequency, and
the reference range for determining whether the examination day is the disordered day is defined for each of the plurality of time periods on a basis of an average value of the amount of body motion in the time period in the plurality of reference days selected from a plurality of days preceding the examination day excluding one or more days determined to be the disordered day, the plurality of reference days being selected in order of closeness to the amount of body motion in the time period on the examination day, starting with a closest day first.

6. A dementia information output apparatus, comprising:
an acquisition circuit that acquires an amount of body motion of a user;
a determining circuit that determines a likelihood that the user is developing a mild dementia on a basis of a variability degree, wherein the variability degree indicates a degree by which the amount of body motion varies in each time period of a plurality of time periods of a day over a plurality of days, respectively; and
an outputting circuit that outputs dementia information indicating the likelihood determined by the determining circuit, wherein:
a timing and a duration of each of the plurality of time periods are common to each of the plurality of days,
the variability degree is determined for each time period of the plurality of time periods over the plurality of days,
the variability degree in each time period of the plurality of time periods corresponds to a variation coefficient defined as a ratio of a standard deviation of the amount of body motion in the time period in a plurality of days to an average value of the amount of body motion in the time period in the plurality of days,
the determining circuit:
(i) acquires, for each period of a plurality of examination periods that each are a period of two or more days, a variation coefficient of each time period of the plurality of time periods in an examination period to acquire a plurality of variation coefficients of the plurality of time periods in the examination period, and acquires an integrated variation coefficient by integrating the plurality of acquired variation coefficients;
(ii) determines whether the integrated variation coefficient of the examination period is within a reference range defined with respect to the integrated variation coefficient of the examination period; and
(iii) determines the likelihood to be higher when it is determined that the integrated variation coefficient of the examination period is not within the reference range defined with respect to the integrated variation coefficient of the examination period than when the integrated variation coefficient of the examination period is determined to be within the reference range, and
the reference range defined with respect to the integrated variation coefficient of the examination period is defined on a basis of an average value and a standard deviation of a plurality of reference variation coefficients selected from a plurality of integrated variation coefficients of a plurality of examination periods preceding the examination period excluding one or more integrated variation coefficients determined to not be within the reference range defined for each of the one or more integrated variation coefficients.

7. The dementia information output apparatus according to claim 6, wherein
the determining circuit determines the likelihood to be higher as the variation coefficient of each of the plurality of time periods becomes higher.

8. A dementia information output apparatus, comprising:
an acquisition circuit that acquires an amount of body motion of a user;
a determining circuit that determines a likelihood that the user is developing a mild dementia on a basis of a variability degree, wherein the variability degree indicates a degree by which the amount of body motion varies in each time period of a plurality of time periods of a day over a plurality of days, respectively; and
an outputting circuit that outputs dementia information indicating the likelihood determined by the determining circuit, wherein:
a timing and a duration of each of the plurality of time periods are common to each of the plurality of days,
the variability degree is determined for each time period of the plurality of time periods over the plurality of days,
the variability degree in each time period of the plurality of time periods corresponds to a variation coefficient defined as a ratio of a standard deviation of the amount of body motion in the time period in a plurality of days to an average value of the amount of body motion in the time period in the plurality of days, the determining circuit:
(i) acquires, for each period of a plurality of examination periods that each are a period of two or more days, a variation coefficient of each time period of the plurality of time periods in an examination period to acquire a plurality of variation coefficients of the plurality of time periods in the examination period, and acquires an integrated variation coefficient by integrating the plurality of acquired variation coefficients;
(ii) determines whether the integrated variation coefficient of the examination period is within a reference range defined with respect to the integrated variation coefficient of the examination period; and
(iii) determines the likelihood to be higher when it is determined that the integrated variation coefficient of the examination period is not within the reference range defined with respect to the integrated variation coefficient of the examination period than when the integrated variation coefficient of the examination period is determined to be within the reference range, and the reference range defined with respect to the integrated variation coefficient of the examination period is defined on a basis of an average value of a plurality of reference variation coefficients selected from a plurality of integrated variation coefficients of a plurality of examination periods preceding the examination period excluding one or more integrated variation coefficients determined to not be within the reference range defined for each of the one or more integrated variation coefficients, the plurality of reference variation coefficients being selected in order of closeness to the integrated variation coefficient of the examination period, starting with a closest coefficient first.

9. A non-transitory computer-readable recording medium having a control program recorded thereon for causing a microprocessor included in a dementia information output apparatus to execute dementia information output processing which includes:

acquiring an amount of body motion of a user from an acquisition circuit included in the dementia information output apparatus;

determining a likelihood that the user is developing a mild dementia on a basis of a variability degree, wherein the variability degree indicates a degree by which the amount of body motion varies in each time period of a plurality of time periods of a day over a plurality of days, respectively; and outputting, from an outputting circuit included in the dementia information output apparatus, dementia information indicating the likelihood determined in the determining, wherein:

the microprocessor executes the dementia information output processing according to the control program, a timing and a duration of each of the plurality of time periods are common to each of the plurality of days, the variability degree is determined for each time period of the plurality of time periods over the plurality of days, the variability degree in each time period of the plurality of time periods corresponds to whether the amount of body motion in the time period of each of the plurality of days is within or not within a reference range defined on a basis of the amount of body motion in the time period in a plurality of reference days, in the determining, one or more disordered days are determined, the one or more disordered days each being a day in which a number of time periods in which the amount of body motion is not within the reference range is larger than a threshold value, in the determining, the likelihood is determined on a basis of an occurrence frequency of the one or more disordered days, in the determining, the occurrence frequency of the one or more disordered days is acquired by determining, for each of a plurality of examination days, whether an examination day is a disordered day, and the likelihood on a basis of the acquired occurrence frequency is determined, and the reference range for determining whether the examination day is the disordered day is defined for each of the plurality of time periods on a basis of an average value and a standard deviation of the amount of body motion in the time period in the plurality of reference days selected from a plurality of days preceding the examination day excluding one or more days determined to be the disordered day.

* * * * *